United States Patent
Vianu et al.

(10) Patent No.: US 11,423,538 B2
(45) Date of Patent: Aug. 23, 2022

(54) COMPUTER-IMPLEMENTED MACHINE LEARNING FOR DETECTION AND STATISTICAL ANALYSIS OF ERRORS BY HEALTHCARE PROVIDERS

(71) Applicant: Covera Health, New York, NY (US)

(72) Inventors: Ron Vianu, New York, NY (US); Tarmo Henrik Aijo, New York, NY (US); James Robert Browning, Vauxhall, NJ (US); Xiaojin Dong, Kew Gardens, NY (US); Bryce Eron Eakin, Astoria, NY (US); Daniel Robert Elgort, New York, NY (US); Richard J. Herzog, New York, NY (US); Benjamin L. Odry, West New York, NJ (US); JinHyeong Park, Princeton, NJ (US); Benjamin Sellman Suutari, New York, NY (US); Gregory Allen Dubbin, New York, NY (US)

(73) Assignee: Covera Health, New York, NY (US)

( * ) Notice: Subject to any disclaimer, the term of this patent is extended or adjusted under 35 U.S.C. 154(b) by 323 days.

(21) Appl. No.: 16/849,442

(22) Filed: Apr. 15, 2020

(65) Prior Publication Data

US 2020/0334809 A1 Oct. 22, 2020

Related U.S. Application Data

(63) Continuation-in-part of application No. 16/386,006, filed on Apr. 16, 2019.

(51) Int. Cl.
*G06T 7/00* (2017.01)
*G06T 7/10* (2017.01)
(Continued)

(52) U.S. Cl.
CPC .......... *G06T 7/0012* (2013.01); *G06K 9/6256* (2013.01); *G06N 3/0445* (2013.01);
(Continued)

(58) Field of Classification Search
USPC ......... 382/100–134, 154–160; 704/231–259; 706/1–21
See application file for complete search history.

(56) References Cited

U.S. PATENT DOCUMENTS

| | | | |
|---|---|---|---|
| 2009/0204436 A1* | 8/2009 | Thorne | G16H 10/60 705/7.42 |
| 2014/0278448 A1* | 9/2014 | Sadeghi | G06Q 10/10 705/2 |

(Continued)

FOREIGN PATENT DOCUMENTS

| | | |
|---|---|---|
| WO | 2017151757 A1 | 9/2017 |
| WO | 2017152121 A1 | 9/2017 |

(Continued)

OTHER PUBLICATIONS

International Preliminary Report on Patentability in related international application No. PCT/2020/028279 dated Jul. 20, 2021.

(Continued)

*Primary Examiner* — Marcellus J Augustin
(74) *Attorney, Agent, or Firm* — Polsinelli, P.C.

(57) ABSTRACT

For training data pairs comprising training text (a radiological report) and training images (radiological images associated with the radiological report), a first encoder network determines word embeddings for the training text. A concept is generated from the operation of layers of the first encoder network, which is regularized by a first loss between the generated concept and a labeled concept for the training text. A second encoder network determines features for the training image. A heatmap is generated from the operation of (Continued)

layers of the second encoder network, which is regularized by a second loss between the generated heatmap and a labeled heatmap for the training image. A categorical cross entropy loss is calculated between a diagnostic quality category (classified by an error encoder) and a labeled diagnostic quality category for the training data pair. A total loss function comprising the first, second, and categorical cross entropy losses is minimized.

21 Claims, 11 Drawing Sheets

(51) Int. Cl.
| | | |
|---|---|---|
| *G06K 9/62* | (2022.01) | |
| *G06N 3/02* | (2006.01) | |
| *G06N 3/04* | (2006.01) | |
| *G06V 10/98* | (2022.01) | |
| *G06V 10/82* | (2022.01) | |
| *G06V 30/40* | (2022.01) | |
| *G06V 30/32* | (2022.01) | |
| *G06V 30/12* | (2022.01) | |
| *G06N 3/08* | (2006.01) | |
| *G16H 30/20* | (2018.01) | |

(52) U.S. Cl.
CPC ............. *G06V 10/82* (2022.01); *G06V 10/98* (2022.01); *G06V 10/993* (2022.01); *G06V 30/133* (2022.01); *G06V 30/333* (2022.01); *G06V 30/40* (2022.01); *G06K 9/6215* (2013.01); *G06N 3/084* (2013.01); *G06T 2207/20081* (2013.01); *G06T 2207/20084* (2013.01); *G06V 2201/03* (2022.01); *G16H 30/20* (2018.01)

(56) References Cited

U.S. PATENT DOCUMENTS

| | | | |
|---|---|---|---|
| 2018/0137244 A1* | 5/2018 | Sorenson | G16H 30/20 |
| 2019/0197358 A1* | 6/2019 | Madani | G06K 9/6272 |
| 2019/0313963 A1* | 10/2019 | Hillen | G06N 3/0454 |

FOREIGN PATENT DOCUMENTS

| | | | | |
|---|---|---|---|---|
| WO | 2018011432 A1 | 1/2018 | | |
| WO | WO-2018011432 A1 * | 1/2018 | ........... | G06F 19/321 |

OTHER PUBLICATIONS

International Search Report and Written Opinion in corresponding international application No. PCT/2020/028279 dated Jun. 24, 2020.

"Predicting Diagnostic Error in Radiology Via Eye-Tracking and Image Analytics: Preliminary Investigation in Mammography", Medical Physicals, vol. 40, No. 10, Sep. 11, 2013.

Written Opinion of the International Preliminary Examining Authority in corresponding international application No. PCT/2020/028279 dated Oct. 28, 2020.

* cited by examiner

12/01/2017: MRI LUMBAR SPINE WITHOUT CONTRAST

CLINICAL INDICATION: Low back pain radiating down right leg. History of lumbar spine surgery. Injury dated August 26, 1966. (M54.5)

COMPARISON: None.

TECHNIQUE: T1 and T2 weighted sequences through the lumbar spine were obtained without intravenous contrast.

FINDINGS: There seem to be five non-rib-bearing lumbar-type vertebral bodies. Vertebral body height is maintained. Vertebral body marrow signal is normal. There is mild intervertebral disc space narrowing at the L4-5 level. Mild disc desiccation is also seen throughout the lumbar spine. There is no abnormal STIR signal to indicate edema. The conus terminates at the L1 vertebral body. The distal cord is normal in signal and diameter. Individual disc levels are as follows:

T12-L1: Mild posterior longitudinal ligament thickening. No disc bulge. No canal or neural foraminal narrowing.

L1-2: Mild broad-based disc bulge with moderate bilateral facet hypertrophy which causes mild AP canal narrowing as well as mild bilateral neural foraminal narrowing.

L2-3: Mild broad-based disc bulge with moderate bilateral facet hypertrophy causing mild AP canal and mild bilateral neural foraminal narrowing.

L3-4: At this level, there has been probable postsurgical change. Mild bilateral neural foraminal narrowing is present.

COMPUTER-IMPLEMENTED MACHINE LEARNING FOR DETECTION AND STATISTICAL ANALYSIS OF ERRORS BY HEALTHCARE PROVIDERS

CROSS-REFERENCE TO RELATED APPLICATIONS

This application claims the benefit of priority to U.S. patent application Ser. No. 16/386,006 filed Apr. 16, 2019 and entitled "COMPUTER-IMPLEMENTED DETECTION AND STATISTICAL ANALYSIS OF ERRORS BY HEALTHCARE PROVIDERS," the disclosure of which is herein incorporated by reference in its entirety.

TECHNICAL FIELD

The present disclosure relates generally to computer-implemented machine learning systems and methods that are programmed to classify digital image data alone or in combination with unstructured text data, and more specifically pertains to machine learning systems and methods for diagnostic error detection.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section. Further, it should not be assumed that any of the approaches described in this section are well-understood, routine, or conventional merely by virtue of their inclusion in this section.

In present healthcare practices, digital images and written reports, the latter typically from dictation, often serve as a basis of diagnostic assessment. Radiology is one example of a field in which images of patient anatomy, and dictated records of assessment by radiologists, often serve as core records reflecting a diagnosis. However, the interpretation of digital images is often complex, requiring significant medical and anatomical knowledge as well as an ability to detect subtle or complicated patterns of information in the correct context, and therefore the radiology field has a non-zero error rate, in which patients have had their diagnostic image data interpreted incorrectly, leading to the wrong diagnosis. The result can have a significant impact on patient comfort, care patterns, treatment outcomes and costs. For example, an erroneous diagnosis could lead to preparation for or performance of a surgical procedure that is unnecessary.

Some diagnostic errors result from deficiencies in a radiologist's skill in interpreting image data, other diagnostic errors result from differences in the communication of diagnostic information in written or dictated diagnostic reports. It is commonplace for different radiology practitioners to express a diagnosis in multiple different ways in writing, or with arcane or incorrect terms; some of these variations will correctly express a patient's diagnosis and many will convey an erroneous or misleading diagnosis.

A wide variety of diagnostic errors and quality issues occur with varying prevalence rates in patient exams. Examples of categories of diagnostic errors include: (1) false positive reporting of a diagnostic finding, (2) false negative reporting of a diagnostic finding, (3) errors in which a finding is "overcalled" or graded as being overly severe, or (4) errors in which a finding is "undercalled" or graded as being too minor. Other quality issues, related to communication issues in the report, can include the following categories: (1) findings that are reported in an overly equivocal manner, (2) findings that are reported in an overly vague manner, (3) findings that are reported with inappropriate emphasis, (4) inappropriate or lack of comparisons with prior diagnostic studies, (5) inappropriate or lack of inclusion of relevant standard measures (e.g. not using the Breast Imaging Reporting and Data System or BI-RADS scoring system for mammogram reports), or (6) inappropriate or lack of follow-up recommendations. Finally, diagnostic radiology exams can also suffer from technical errors and quality issues that can include: (1) poor image quality (e.g. low signal-to-noise ratio), (2) images degraded or obscured by patient motion or other artifacts, (3) poorly configured exam protocols (e.g. an MRI exam conducted without collecting images that have a necessary image contrast setting or images collected with resolution that is too low), or (4) poor anatomical coverage of the images.

Assessing the accuracy of diagnoses and presence of specific types of errors is difficult for patients and other stakeholders, including other physicians involved in a patient's care and healthcare payers. Presently, most efforts to assess the accuracy of a diagnosis rely on obtaining a second opinion from another radiologist or medical professional and then comparing the second opinion with the first opinion. While a diagnostic accuracy assessment could be based upon favoring the second opinion of an authoritative expert, the healthcare system might not be well-served if correct diagnoses only can be achieved by a subset of experts. Furthermore, authoritative experts are themselves fallible and pathological assessment always involves a measure of subjectivity, so it may be difficult to determine if variation across the two diagnoses represent evidence of diagnostic errors present in at least one diagnosis or if the variation represents multiple ways of stating the same diagnosis. Seeking a third or multiple additional opinions on a given patient's diagnosis does not alleviate this issue and is likely prohibitive due to logistics or cost for most patients.

Therefore, there is a long-felt need in the field for a standardized, robust, and quantitative method for assessing the accuracy of patients' diagnoses and the diagnostic accuracy and error rates achieved by radiology providers. However, this requires a scalable system for standardizing multiple aspects of the diagnostic quality assessment process, including, (1) the diagnostic interpretation of image data, (2) the documentation of diagnostic findings in dictated or written diagnostic reports, and (3) the categorization of various diagnostic errors and quality issues.

While extensive medical records are usually developed for each patient in digital electronic form, typically much of the data is unstructured; examples are the digital medical images and dictated diagnostic reports, both of which are non-standardized across patient exams and not readily interpretable by machines or computers. While more structured dictation could be provided, it is an imperfect approach that is unlikely to be adopted on a widespread basis. Additional tools or systems are required to transform the unstructured information in medical images and diagnostic reports into standardized data that can be leveraged for assessment of diagnostic accuracy, error rates, and quality.

Since a multitude of diagnostic errors and related quality issues are possible in the context of most diagnostic imaging exams, it can be valuable to prioritize the specific types of diagnostic findings and diagnostic errors that a diagnostic accuracy and quality assessment system will target for evaluation. One approach to prioritization is to identify general aspects of diagnoses that are clinically meaningful for patients' care patterns and/or outcomes and achieve high degrees of agreement between radiologist. Since perfect agreement between radiologists is not likely in any category of diagnostic finding or diagnostic error, and the levels of agreement exhibit a wide variability across categories of diagnostic findings and errors, is can be valuable for a diagnostic accuracy and quality assessment system to be able to appropriately quantify the amount of agreement that radiologists exhibit in each category of diagnostic finding and error under evaluation.

Key outputs from diagnostic accuracy and quality assessment systems include estimates of the accuracy rates and error rates that are achieved by a radiology provider under evaluation. However, if estimates of accuracy rates and error rates are directly based on data generated by independent radiologists who use a standardized process for identifying and characterizing selected diagnostic findings and diagnostic errors, the estimates will themselves not be accurate or reliable due to inter-radiologist variability.

Stakeholders in the healthcare ecosystem have developed an increased interest in quantitative and reliable healthcare quality metrics that are highly correlated with patient outcomes, patient comfort or quality of life, and costs. However, since not all diagnostic errors and quality issues have the same impact on downstream patient care patterns or patient outcomes, straightforward estimates of diagnostic accuracy rates or error rates may not represent a valuable quality metric.

When using a diagnostic accuracy and quality assessment system to evaluate multiple distinct providers, it is critical to account for the fact that different providers often care for very different patient populations. It may be inappropriate to use unadjusted estimates of diagnostic accuracy rates or error rates as standardized and generalizable measures of radiology care quality. A quality assessment system that can be used across a diverse population of providers will usually need to include some adjustment for differences between the relevant patient populations.

Furthermore, there is an acute need for computer-implemented techniques that can generate data representing the quality or accuracy of medical diagnoses in a robust and scalable manner. In some instances, institutions have attempted to replace or supplement radiologists, in the context of their clinical workflow as they perform initial interpretations of image data and generate diagnostic reports, with machine-executed image recognition and interpretation systems. These systems are programmed to inspect images and flag abnormalities. However, known systems typically identify too many false positives, or work only with abnormalities that are straightforward to find in an image, and therefore they do not add significant value to the ecosystem in this capacity.

Computer-implemented image interpretation and medical report interpretation technologies have not been developed, expanded, or adapted for use as part of a diagnostic accuracy and quality assessment system. The technical performance and design requirements for these technologies are different in this distinct application domain. In the context of an initial interpretation of image data to support (or replace) a radiologist as they generate a specific patient's diagnostic report, a computer-implemented image interpretation system will need to achieve high sensitivity, high specificity, and an ability to target a wide range of diagnostic finding types. In the context of a diagnostic accuracy and quality assessment system that is supplemented with or solely executed by a computer-implemented image interpretation system, which will also need to be integrated with a computer-implemented medical report interpretation system, there are more relaxed performance requirements with respect to sensitivity, specificity, and variety of targeted diagnostic finding types. The reason for this relaxation of performance requirements is that, as long as the sensitivity and specificity performance levels of the computer implanted systems is quantified, it is still possible calculate robust and reliable estimates of the overall diagnostic accuracy and error rates, along with appropriate confidence intervals around these estimates, that radiology providers achieve when caring for populations of patients.

SUMMARY OF THE INVENTION

According to an aspect of the present disclosure, provided are systems and methods for training a machine learning network for diagnostic quality assessment. The method comprises, for each given training data pair of a plurality of training data pairs, where each given training data pair comprises at least a training text derived from a radiological report and a training image derived from a radiological exam image associated with the radiological report, training a diagnostic quality assessment machine learning network by: determining, using a first encoder network, word embeddings for the training text; generating, using a concept generator coupled to one or more layers of the first encoder network, a generated concept based on the operation of the one or more layers in determining the word embeddings; regularizing the first encoder network by calculating a first loss between the generated concept and a labeled concept for the training text; determining, using a second encoder network, features for the training image; generating, using a heatmap generator coupled to one or more layers of the second encoder network, a generated heatmap based on the operation of the one or more layers in determining the features; regularizing the second encoder network by calculating a second loss between the generated heatmap and a labeled heatmap for the training image; classifying, via an error encoder, the given training data pair into a determined diagnostic quality category; calculating a categorical cross entropy loss between the determined diagnostic quality category and a labeled diagnostic quality category for the given training data pair; and minimizing a total loss function for the given training data pair, the total loss function comprising at least the first loss, the second loss, and the categorical cross entropy loss.

In an aspect of the disclosure, the training text is a section of text obtained from a radiological report, wherein the section of text corresponds to an identified anatomical region or pathological feature discussed in the radiological report.

In a further aspect of the disclosure, the training image is a section obtained from a sequence of one or more radiological exam images from which the radiological report was prepared.

In a further aspect of the disclosure, for a given training data pair, the training text and the training image are associated with the same anatomical region or pathological feature.

In a further aspect of the disclosure, the same anatomical region or pathological feature is a motion segment of the lumbar spine.

In a further aspect of the disclosure, one or more of the plurality of training data pairs are obtained from a database of structured checklists corresponding to medical diagnostic data, the medical diagnostic data including radiological reports and radiological exam images.

In a further aspect of the disclosure, the first encoder network is configured as a recurrent neural network, an ordered neuron LSTM (Long short-term memory), or a Transformer based model trained specifically on a corpus of radiology report text.

In a further aspect of the disclosure, the labeled concept for a given training text includes an indication of one or more of: an identified pathology, a location of the identified pathology, and a severity of the identified pathology, as contained within the given training text.

In a further aspect of the disclosure, the second encoder network is a densely connected convolutional neural network (DenseNet) or a residual neural network (ResNet) adapted to the anisotropy and intensity distribution of radiology exam images.

In a further aspect of the disclosure, the generated heatmap is an attention heatmap determined from the one or more layers of the second encoder network while the second encoder network generates features for the training image; and the labeled heatmap is an annotation corresponding to one or more anatomical features or pathological features as located within the training image.

In a further aspect of the disclosure, the heatmap generator comprises a decoder for performing a specific segmentation of the training image; and the labeled heatmap is an annotated segmentation corresponding to one or more anatomical features or pathological features as located within the training image.

In a further aspect of the disclosure, the determined diagnostic quality category is selected from a set of diagnostic quality categories including 'Agree', 'Overcall', 'Undercall', and 'Missed'.

In a further aspect of the disclosure, training the diagnostic quality assessment machine learning network on the given training data pair further comprises: regularizing the first encoder network by minimizing a first BCE (binary cross entropy) loss between a labeled pathology for the training text and a generated pathology for the training text, the generated text pathology output by an NLP (natural language processing) pathology classifier over the word embeddings of the first encoder network; regularizing the second encoder network by minimizing a second BCE loss between a labeled pathology for the training image and a generated pathology for the training image, the generated image pathology output by an image pathology classifier over the features of the second encoder network; and the total loss function further comprises the first BCE loss and the second BCE loss.

In a further aspect of the disclosure, the labeled pathology for the training text is ground-truth pathology information contained within the training text, independent from its specific textual expression; and the labeled pathology for the training image is ground-truth pathology information present in the training image, wherein the ground-truth pathology information for a given training image is determined as a consensus obtained from one or more expert reviews of the given training image.

In a further aspect of the disclosure, the labeled pathology for the training image is generated automatically based on accessing one or more structured checklists generated in response to receiving a user input representing of the one or more expert reviews of the given training image.

In a further aspect of the disclosure, training the diagnostic quality assessment machine learning network on the given training data pair further comprises: providing, to a Siamese function, an input comprising the word embeddings determined for the training text by the first encoder network and the image features determined for the training image by the second encoder network; calculating, using the Siamese function, a Siamese distance between the word embeddings and the image features; calculating, using a Siamese error encoder, a Siamese loss between the Siamese distance and a Siamese label, the Siamese label indicating an extent to which the training text and training image of the given training data pair agree or disagree; and minimizing the Siamese loss to increase a distance between training text and training images that disagree and to decrease a distance between training text and training images that agree.

In a further aspect of the disclosure, the Siamese loss is a multi-task loss; the error encoder classifies the given training data pair into the determined diagnostic quality category based at least in part on the Siamese distance output by the Siamese function; and the total loss function for the given training data pair further includes the Siamese loss.

In a further aspect of the disclosure, back propagating the Siamese loss to adjust one or more parameters of the first encoder network and the second encoder network; and configuring the Siamese error encoder as a controller to the error encoder, wherein the error encoder classifies the given training data pair into the determined diagnostic quality category based on the word embeddings from the first encoder network and the image features from the second encoder network.

In a further aspect of the disclosure, the Siamese error encoder acts as a controller to the error encoder by causing the error encoder to regress to an estimated diagnostic error on the basis of the Siamese distance between the word embeddings and the image features.

In a further aspect of the disclosure, the method further comprises providing at least the determined diagnostic error from the error encoder, the word embeddings from the first encoder network, and the image features from the second encoder network, to a clinical significance encoder; and regressing, using the clinical significance encoder, to an estimated clinical significance of the determined diagnostic error, wherein the clinical significance encoder is configured as a regressor network having a sigmoid activation function.

In a further aspect of the disclosure, the method further comprises providing one or more clinical references to a clinical controller of the diagnostic quality assessment machine learning network, the clinical references including one or more of patient age, patient weight, and patient history of previous related pathologies; and generating, from the one or more clinical references and via the clinical controller, a feature vector to control the second encoder network.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which:

FIGS. 4A-B illustrate an example flowchart of a pre-processing pipeline for input radiological images and/or input radiological reports;

DETAILED DESCRIPTION

Figure 1:
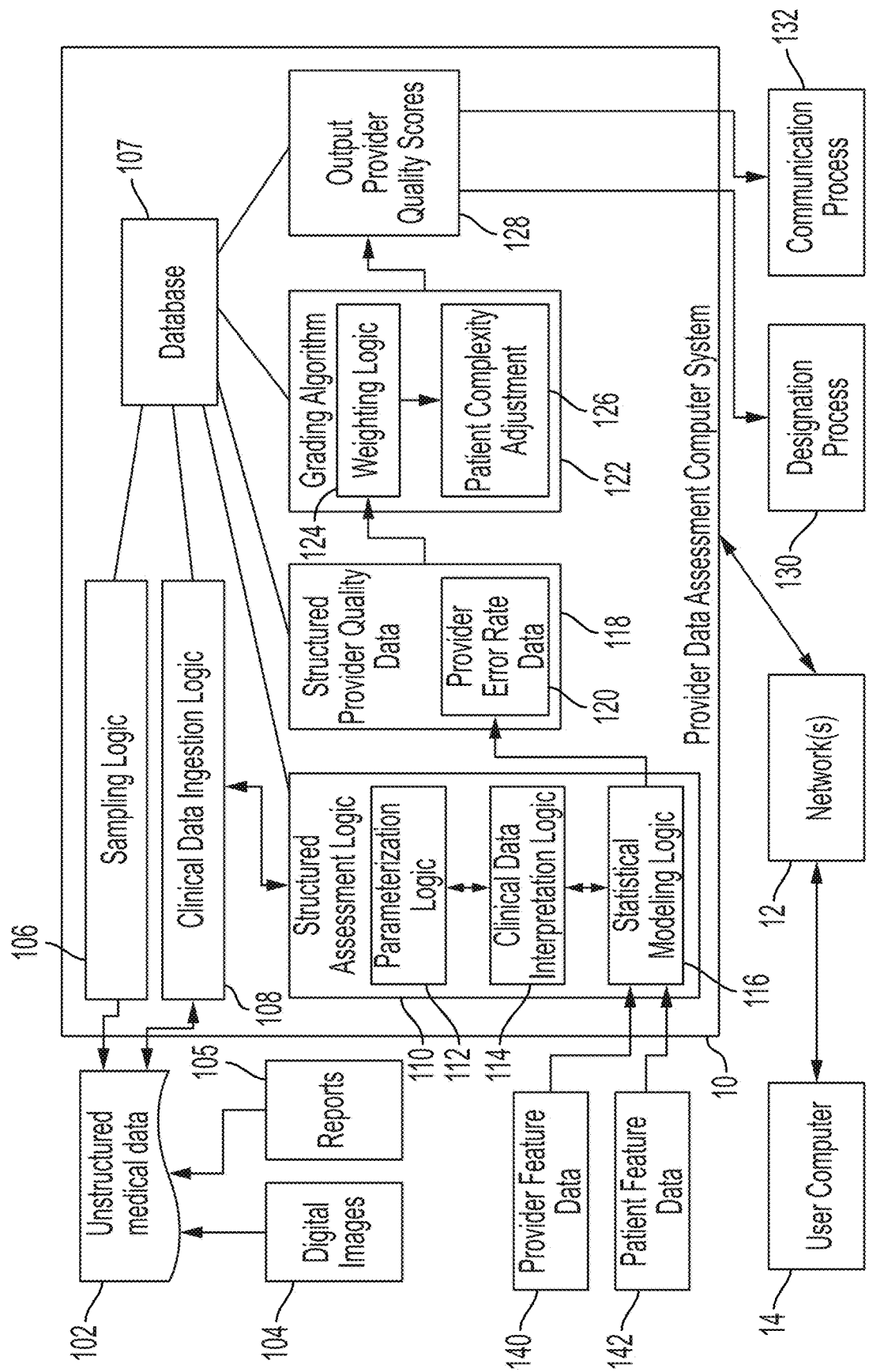
FIG. 1 illustrates an example of functional elements and data flows in a distributed computer system that may be used to implement one embodiment of provider assessment processing.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Additional features and advantages of the disclosure will be set forth in the description which follows, and in part will be obvious from the description, or can be learned by practice of the herein disclosed principles. It will be appreciated that for simplicity and clarity of illustration, where appropriate, reference numerals have been repeated among the different figures to indicate corresponding or analogous elements. The description is not to be considered as limiting the scope of the embodiments described herein.

Using various machine learning techniques and frameworks, it is possible to analyze data sets to extract patterns and correlations that may otherwise have not been apparent when subject to human analysis alone. Using carefully tailored training data inputs, a machine learning system can be manipulated to learn a desired operation, function, or pattern. The performance of a machine learning system largely depends on both the quality and the quantity of these carefully tailored data inputs, also known as training data. Machine learning is capable of analyzing tremendously large data sets at a scale that continues to increase; however, the ability to build and otherwise curate appropriately large training data sets has lagged and continues to be a major bottleneck in implementing flexible or real-time machine learning systems.

A detailed description of example methods for machine learning networks for automated assessment of diagnostic quality, as referenced above, is provided below in Sections 7 and 8. Section 7 provides a general overview of an example machine learning network for diagnostic quality assessment. Section 8 provides architecture and training details of the example machine learning network for diagnostic quality assessment.

1. General Overview

In an embodiment, a system for quantifying diagnostic radiology errors uses structured and standardized exam reviews that are performed by independent radiologists to create a repository of clinically meaningful attributes of radiology images and radiology reports. Digital analysis of the attributes yields an objective truth source for any diagnosis that can be associated with digital images of anatomy or other physical features of the subject as well as an objective truth source for any diagnostic error or quality issue associated with the manner in which diagnoses were described or omitted from the radiology report.

A modified embodiment may supplement the attributes, or categories of attributes, with reliable measures of confidence or probability of correctness. These reliable measures of confidence or probability of correctness may be generated by statistical analysis of the variances across the attributes in reports that were generated by the radiologists performing structured and standardized radiology exam reviews. In some cases, the radiologists performing structured and standardized radiology exam reviews will independently review the same underlying radiology exam and generate reports that will contribute to the analysis of variance.

The techniques herein are most suitable for assessing diagnostic accuracy, errors, and/or quality related to pathology or disease that is subject to generally good agreement among experts with respect to physical features that are present, location, size and so forth.

In some embodiments, the system for quantifying diagnostic radiology errors will be optimized to generate accurate quantitative measures of diagnostic error rates and quality issues related to specific radiology providers that are selected for assessment and their associated performance with respect to specific pathologies and diseases. These quantitative measures of diagnostic error rates may be aggregated to varying levels of anatomical detail, for example: (1) a combined measure representing the rate of any error that a radiology provider makes in the context of diagnostic knee MRI exams, or (2) a more narrow-scope measure representing the rate of any error that a radiology provider makes pertaining to an accurate diagnosis of meniscal tears within knee MRI exams. These quantitative measures of diagnostic error rates may also be aggregated to varying levels of diagnostic error types, for example: (1) a measure representing the rate of any false positive errors that a radiology provider makes in the context of diagnostic imaging exams, or (2) a measure representing the rate of any errors in which a finding is "undercalled", or mistakenly graded as being too minor, that a radiology provider makes in the context of diagnostic imaging exams. Finally, these quantitative measures of diagnostic error rates may be aggregated to varying levels of within a radiology provider organization, for example: (1) a measure representing the rate of any diagnostic error that an individual radiologist makes in the context of selected diagnostic imaging exam types, or (2) a combined measure representing the rate of any error that a group of radiologists who practice together at single radiology facility make in the context of selected diagnostic imaging exam types.

In some embodiments, the measures of diagnostic error rates will be entirely based on the empirical diagnostic error data and attributes that are produced by the independent radiologists who perform standardized reviews of the exams performed by the radiology providers under review. In some embodiments, the measures of diagnostic error rates will be based, all or in part, on statistical modeling, including hierarchical Bayesian statistical modeling, of the empirical diagnostic error data and attributes.

Some embodiments of the system for quantifying diagnostic radiology errors will also be optimized to generate measures of diagnostic quality that are modified versions of radiology provider error rates. These measures of diagnostic quality may be weighted combinations of specific diagnostic errors, such that the weighting may represent the relative likelihood that a specific type of diagnostic error will have an impact on patients' treatment pathways, clinical outcomes, or costs of treatment and subsequent care. The method for combining the various diagnostic error rates into the new quality measure may involve weighted averaging, linear or non-linear statistical modeling, or machine learning. The assignment of weights that represent the likelihood that specific types of diagnostic errors will have a clinical impact on patients may be accomplished by: (1) capturing additional data elements during the standardized diagnostic exam reviews, (2) stand-alone assessments by radiologist or other medical experts of the likely clinical impact of specific types of diagnostic errors, or (3) analysis of historical medical records of patients in combination with diagnostic error data to estimate the correlation of specific diagnostic errors or providers with specific error rates and impacts to patients' treatment patterns, costs, and outcomes.

In some embodiments, the diagnostic error data and attributes that are generated through standardized review of imaging exams will be supplemented with additional data and attributes about the radiology providers under evaluation. Examples of these supplementary data and attributes may include: (1) radiologists' educational history, including fellowship training status, (2) radiologists' years of practice, (3) radiologists' historical exam volume and case mix, (4) radiology facilities' imaging equipment, or (5) radiology facilities' imaging exam protocol configurations. This supplementary data and attributes may be leveraged by the system to: (1) generate measures of diagnostic error rates or weighted diagnostic error rates with improved accuracy, precision, or narrower confidence intervals; or (2) to generate predicted measures of diagnostic error rates or weighted diagnostic error rates for radiology providers which have not had any of their imaging exams subjected to standardized reviews and for whom only the supplementary data elements and attributes are available. The methodologies that can be employed to leverage the supplementary radiology provider data and attributes in this way involves modeling the correlations between these new supplementary data elements and the data elements related to diagnostic errors and quality issues that are generated by the standardized imaging exam reviews; the quantitative methodologies that are used in this context may include Bayesian or log-linear statistical modeling or machine learning techniques.

In some embodiments the system for quantifying diagnostic radiology errors will also be optimized to generate measures of diagnostic quality that are also adjusted for patient complexity, such that radiology providers may be penalized less for having higher rates of diagnostic errors when caring for a population of more complex patients and vice versa. To quantify the complexity of individual patients and populations of patients that are associated with the various radiology providers under evaluation, the system may leverage combination of data from: standardized reviews of imaging exams, billing or claims data, patient demographic data, or other data extracted from electronic medical records. The system may employ Bayesian or log-linear statistical modeling, linear or non-linear regression, or machine learning methodologies to achieve the patient complexity adjustment of the diagnostic quality measures.

In one embodiment, patient complexity is adjusted for using a two-step process. In step one, diagnostic error rate estimates for each radiology provider under evaluation are modeled as conditional probabilities, i.e. diagnostic errors rate for each provider are estimated conditional on the presence of specific medical conditions and severities across the patient population observed for the radiology provider. We denote the computed estimates (e.g., via regression) of these conditional probabilities as $P_r(Y|P=p)$, where Y is a variable representing diagnostic error rate and $P=p$ is a specific medical condition and severity; and we further denote the distribution of all medical conditions and severities observed for the radiology provider as $f(P=p)$, at each level of which we have the aforementioned estimated conditional probability.

In step two, a data set is defined that represents a reference patient population $f(P^*=p^*)$, which has a fixed distribution of medical conditions and severities (this distribution can be modeled using empirical observations or a reference patient population can be created with an arbitrary distribution of medical conditions and severities for this purpose). The diagnostic error rates estimated for each radiology provider, as conditional probabilities from step 1, can then be evaluated with respect to this distribution, i.e., $E[f(Y'|P=p=p^*)|f(P^*=p^*)]$ can be calculated for different providers, and these results can be directly compared to evaluate relative provider performance with respect to the same reference patient population. This two-step process allows an "apples to apples" comparison of diagnostic error rates across radiology providers that is not confounded by differences in the complexity of the patient population the radiology providers happen to be observed treating. In some embodiments the attributes generated by the standardized exam reviews are used to train computer-implemented machine learning algorithms, for example recurrent neural networks or deep learning algorithms, such that the computer-implemented algorithms can then independently analyze digital radiology images and radiology reports and automatically apply the attributes that are included in the standardized exam reviews. Examples of such machine learning networks for automated diagnostic quality assessment are discussed in greater depth below, in Sections 7 and 8. These computer-implemented machine learning networks and algorithms can be trained to analyze radiology images to identify the presence or absence and severity of the specific pathologies that are assessed by the radiologists when they perform the standardized exam reviews. When analyzing the images, the algorithms may also be trained to generate attributes that describe the technical quality of the images, for example: (1) poor image quality (e.g. low signal-to-noise ratio), (2) images degraded or obscured by patient motion or other artifacts, (3) poorly configured exam protocols (e.g. an MRI exam conducted without collecting images that have a necessary image contrast setting or images collected with resolution that is too low), or (4) poor anatomical coverage of the images. The computer-implemented machine learning networks and algorithms can also be trained to analyze radiology reports to identify the presence or absence of specific diagnostic findings in the reports as well as the severity of the pathologies that are reported. When analyzing the radiology reports, the algorithms may also be trained to generate additional attributes related to the quality of the report, for example: (1) findings that are reported in an overly equivocal manner, (2) findings that are reported in an overly vague manner, (3) findings that are reported with inappropriate emphasis, (4) inappropriate or lack of comparisons with prior diagnostic studies, (5) inappropriate or lack of inclusion of relevant standard measures (e.g. not using the Breast Imaging Reporting and Data System or BI-RADS scoring system for mammogram reports), or (6) inappropriate or lack of follow-up recommendations. Once the algorithm performs its assessment on the images and report associated with a specific patient exam, it will compare its assessment of the pathologies in the images with its assessment of the diagnostic findings present in the radiology report to create attributes that represent the accuracy of the radiology report and any diagnostic errors that exist.

In some embodiments, the computer-implemented algorithm will produce measures of uncertainty for each attribute it generates related to the radiology images, radiology reports, and diagnostic errors. These measures of uncertainty will be based on quantitative assessments of the computer-implemented algorithm's performance in training and validation datasets. The measures of uncertainty may also incorporate measures of the underlying variability in accuracy of the training and validation datasets themselves. As discussed in greater depth below, these measures or other outputs of uncertainty from one or more components of the presently disclosed machine learning network(s) can be expressed as a feature vector, which can then be used as an input feature for the disclosed Bayesian approach to estimating physician's accuracies in diagnosing a pathology.

For example, the same statistical modeling methodologies described above may be applied to the diagnostic error attributes generated by the computer-implemented algorithms, in order to calculate estimates of radiology provider diagnostic error rates and weighted measures of diagnostic error rates and diagnostic accuracy. As described above, some embodiments may supplement the diagnostic error attributes with additional attributes related to radiology provider characteristics in order to generate measures of diagnostic error rates or weighted diagnostic error rates with improved accuracy, precision, or narrower confidence intervals The analytic approaches of embodiments may execute as overnight or background processes at any time after physicians or practitioners generate new radiology images or submit new radiology reports. In some embodiments, the processes described for FIG. 1, FIG. 3 may be executed in real-time immediately after a physician submits a report to provide immediate feedback to the healthcare provider in the form of a quality review or quality report. Or, data indicating errors can be communicated to an administrator, third-party reviewer, or other system or program without direct notification to the primary physician who submitted a report. Or, in yet another alternative, errors may be scored and ranked according to seriousness or severity, and only errors above a threshold severity value may be communicated to the primary physician.

For purposes of illustrating clear examples, certain aspects of this disclosure expressly refer to use in the context of radiology practice. However, the principles of this disclosure and other embodiments may be used in connection with any other kind of healthcare practice and embodiments are not limited to radiology. Furthermore, for purposes of this disclosure, certain embodiments are described using terms having the following definitions:

Location—a region of the human body admitting specific distinct, though perhaps related, pathologies.

Pathology—a well-defined malady, for example, "central canal stenosis of the L2-3 segment in the lumbar spine".

Item—a checklist question engineered to elicit a pathology-specific diagnosis.

Diagnosis—a selected value for an item, such as None, Small, Medium, Large.

Checklist—a collection of items capturing a specific diagnosis for a particular medical discipline or specialty.

Reading provider—a physician or practitioner who is the one providing diagnoses for evaluation.

Reviewing provider—a physician or practitioner who is evaluating the diagnoses of a reading provider after the fact, for accuracy.

Practice—a group of providers that is defined by business or geographic attributes.

Provider—a broad term for a physician, other healthcare practitioner, practice, group or other aggregation.

2. Overview of Example Diagnostic Quality Assessment Framework for Radiology

FIG. 1 illustrates an example of functional elements and data flows in a distributed computer system that may be used to implement one embodiment of provider assessment processing. In an embodiment, computer-implemented processes may be programmed to support assessment of the quality level of radiology providers and practices. Other embodiments may be applied to other medical disciplines.

In one embodiment, a provider data assessment computer system 10 comprises sampling logic 106 which receives unstructured medical data 102 as input, clinical data ingestion logic 108 and structured assessment logic 110 which may receive provider feature data and patient feature data for use in executing statistical modeling operations as further described herein. These functional elements cooperate, under program control as further described functionally herein, to generate structured provider quality data 118, which may be provided as input to a grading algorithm 122 for calculation of output provider quality scores 126. The resulting scores may be provided to or used as part of a designation process 130 and/or communication process 132. A digital database 107 may be programmed to store the unstructured medical data 102 after input as well as the structured provider quality data 118, output provider quality scores 126, feature data 140, 142, and other data such as pathology prevalence data and error data for different fields of specialty.

Computer system 10 may be implemented using one or more distributed or networked computers, services, processes or other software elements hosted using desktop computers, on-premises server computers or cloud computing instances of virtual computing centers. Each of the functional elements of computer system 10 may execute as a separate asynchronous thread, service or method. In some embodiments, multiple instances of functional elements may be provided. For example, structured assessment logic 110 may execute as a plurality of independent instances in a virtualized computer to enable parallel processing of multiple datasets or parts of a single dataset. In some embodiments, aspects of structured assessment logic 110 may be programmed as a SaaS application hosted on a web server to communicate with a browser executed at a user computer 14 that is coupled to computer system 10 directly or indirectly via one or more computer networks 12 or internetworks.

One practical application of computer system 10 is detection and measurement of observed diagnostic error rates for sampling of clinical exams from radiology providers. In an embodiment, sampling logic 106 is programmed to identify which types of exams and how many clinical exams to sample from radiology providers. Exams may be represented in digital images 104, typically associated with reports 105 consisting of digitally stored text, as part of unstructured medical data 102. For example, a particular report among the reports 105 may represent a set of comments or notes on pathological structures that are visible or believed to be visible in one or more associated digital images 104. Thus, reports 105 typically represent physicians' diagnostic findings with respect to corresponding specific digital images 104, and there may be thousands or millions of sets of images and reports for different patients, exams and diagnoses. In some embodiments, sampling logic 106 is programmed to calculate a sample of exams based upon an estimated or measured prevalence of key pathologies and diagnostic errors, combined with specific criteria relating to a particular kind of designation of the provider.

For example, if the unstructured medical data 102 consists of scans of lungs, and data in database 107 indicates that lung scans have a low prevalence of lung cancer pathology as well as a low percentage of diagnostic errors for lung cancer, then the sampling logic 106 may apply a programmed rule to select a relatively high percentage, for example 50%, of all the exams for further analysis. In contrast, a different set of scans with higher pathology prevalence and/or a higher known percentage of diagnostic error might trigger a programmed rule of the sampling logic 106 to select a lower percentage, for example 10%, of all exams in the set for analysis. Furthermore, the resulting percentage or number of exams that are selected by the sampling logic 106 may be weighted or biased by other attributes and data elements in database 107 related to the provider that provided the unstructured medical data 102, for example: pre-existing quality designations or error rate estimates, the provider's patient volumes or cases mixes, or fellowship training status of providers.

In an embodiment, clinical data ingestion logic 108 is programmed to capture raw clinical data. For radiology providers, raw clinical data may comprise medical images, which could be in the form of DICOM files, and diagnostic reports, as represented by digital images 104 and reports 105. Or, digital images 104 may comprise any form of graphical images that are captured in a radiology practice including X-ray, MRI or CT images, digital film or other diagnostic data. Images 104 may be associated with corresponding reports 105, which consist of text in any digitally stored form. As previously noted, embodiments are not limited to radiology and other disciplines may interoperate with the processes herein based on raw clinical data of other types. For other providers, the type of raw clinical data may comprise electronic medical record (EMR) records or files, free-text notes, PDF files scanned from notes or generated from text files such as dictations, non-digital data such as the contents of a paper chart that has been scanned into image form or processed using optical character recognition (OCR), image-based diagnostic tests other than radiology imagery, claims data, billing data, employer-specific work data, audio files such as recordings of consultations or office visits with physicians or transcripts of the audio files, video recordings of surgeries or other interventions or procedures, or data from wearable devices. In some instances, raw clinical data may be partly structured; for example, data files may include metadata such as provider credentials, equipment attributes, length of exam, demographic or diagnostic features of patients.

It will be apparent that with datasets of the foregoing type, determining whether diagnostic errors have occurred, or other aspects of the quality of a diagnosis, cannot be obtained directly from the data. Quality attributes may relate to the technical performance of a diagnostic exam, such as poor-quality images or images that do not sufficiently cover the necessary anatomy. In an embodiment, elements of FIG. 1 are programmed to transform the unstructured raw clinical data described above into at least partly structured data, and structured review procedures and machine-executed statistical analysis are performed to analyze the available data to derive error data and quality score values. Consequently, useful and meaningful values are extracted from previously non-usable data.

In an embodiment, clinical data ingestion logic 108 is programmed to use OCR and natural language processing (NLP) techniques, which may be implemented in external code libraries or web services, to convert unstructured diagnostic report text to structured, machine-readable data. In an embodiment, clinical data ingestion logic 108 is programmed to use image processing libraries or functions to convert medical image data into structured, machine-readable data. For example, clinical data ingestion logic 108 may be programmed to perform image feature identification in digital images 104 and generate output data comprising a graph, tree or list of features that have been identified.

Other functional elements of computer system 10 are programmed to determine what diagnostic errors were made. In radiology, for example, errors could arise from low-quality images, motion artifacts from movement of the patient at the time of capturing an image, poor positioning of anatomy in relation to a camera or scanner, and so forth. In an embodiment, trained primary physicians initially prepare the raw clinical data and images, and secondary reviewers use structured processes to assess features for quality.

In an embodiment, structured assessment logic 110 is programmed with parameterization logic 112 to execute clinical data assessment parameterization. The parameterization logic 112 executes in the context of a set of one or more digital images, from among the digital images 104, that have been reviewed by a primary physician or practitioner and interpreted in a corresponding report from among the reports 105. Thus, a particular report 105 comprises a written interpretation of a set of associated images, completed by a primary physician. The parameterization logic 112 may be programmed to:

A. Select a set of one or more digital images from among the digital images 104 and a corresponding report 105, automatically according to a workflow or order, or based on input from user computer 14. The user computer 14, in this example, is associated with a secondary physician reviewer. In some embodiments, parameterization logic 112 may be programmed to present a list of available images in a graphical user interface with GUI widgets that are programmed to indicate selection of particular images.

B. Present the corresponding report via output to a computer display device of the user computer 14 and wait for user input to interpret the report.

C. Select a structured checklist, from among a plurality of structured checklists that are stored in database 107, that applies to the digital image, a medical field that is associated with the selected digital image, or that is specified in configuration data. Each checklist may be digitally stored in the database 107 as a row of a database table in which columns represent diagnostic dimensions or parameters, and then rendered in a graphical user interface in the form of a checklist under program control; thus, literal storage as a document is not required and digital data structures may be used to represent checklists in storage.

D. Render and display the structured checklist via output to a computer display device of the user computer 14 and wait for user input to respond to items in the checklist in reference to the current digital image. The secondary physician reviewer follows the checklist to detect and measure the prevalence of diagnostic errors and to control the generation of training data for artificial intelligence logic such as a neural network or classifier. The checklist addresses key diagnostic dimensions or parameters in interpretation of the digital images 104 for radiology or other specialties, customized to specific anatomical areas. Checklists may be created and stored in advance for any medical discipline and the key dimensions or parameters of quality of a checklist will reflect that discipline. For example, a checklist may prompt for input from user computer 14 to indicate (a) whether disc herniation is present in the L4-5 lumbar spine and (b) if present, whether it is small, moderate or large. Input from user computer 14 may be stored in database 107 in association with identifiers of a dataset, a particular digital image among the digital images 104, a checklist and a user account. Furthermore, for some disciplines, the use of a checklist with digital image data will not be required and checklists may be assessed based on written reports or text data, as next described.

In an embodiment, the secondary reviewer physician compares their interpretation of the digital images with the original physician's diagnostic report as abstracted by the checklist. The reviewer then uses the checklist and uses GUI widgets generated and displayed by the clinical data interpretation logic 114 to parameterize the level of agreement or disagreement between the reviewer's interpretation and the original interpretation, producing data that describes diagnostic errors. In some embodiments, clinical data interpretation logic 114 may be programmed to presume that the reviewer is correct, but some embodiments may model, under program control, variability of interpretation among reviewers, as further described.

E. Repeat the foregoing steps for all checklists applicable to the current digital image.

F. Return to the first step to process a different digital image or return control to the user computer or another system, program or process.

In this manner, computer-implemented processing may be used to cause database 107 to develop a comprehensive dataset that characterizes issues associated with a large number of digital images associated with exams. In some embodiments, each stored checklist later may be used as a portion of training data for training the statistical modeling logic 116 when implemented as a neural network or classifier. After a training phase, in an evaluation phase, the statistical modeling logic 116 may execute to receive the digital images 104, receive the reports 105, interpret the images according to one or more checklists, interpret the original physician's diagnostic report according to the checklist, compare the machine-generated interpretation of the images to the original physician's diagnostic report, utilizing the checklist to parameterize levels of agreement or disagreement, and generate output data identifying diagnostic errors with associated confidence level values. The statistical modeling logic 116 may receive provider feature data 140 and patient feature data as input to adjust the classification of images and reports, and output error data, based on variable features of providers and patients, as further described in other sections. Broadly, statistical modeling logic 116 executes as a trained classifier to detect errors in unstructured medical diagnostic data after training on similar medical diagnostic data in which errors have been explicitly identified.

One result of processing using the statistical modeling logic in this manner may be provider error date data 120, which may form one component of stored, structured provider quality data 118. In an embodiment, structured provider quality data 118 may be used in several different ways.

A. In an embodiment, the quality data 118 may be provided as input to the grading algorithm 122, which is programmed to use weighting logic 124 and patient complexity adjustment 126 to transform the error data.

In an embodiment, weighting logic 124 applies weight values to quality scores based on a combination of expert clinical input and data-drive insights about outcomes. These factors may be used to calculate weight values to assign to specific diagnostic errors, representing a weight of that error relative to its impact on later clinical care or treatment. Thus, a particular error may have a high weight value if its impact on clinical care or treatment, such as the complexity of a later treatment, patient discomfort or cost is high. Thus, a particular quality score 128 may be adjusted upward or downward based on the weight value associated with the error(s) represented in error rate data 120 that led to the score.

Patient complexity adjustment 126 is programmed to obtain data from database 107 for patient complexity including but not limited to demographic data such as age and sex, and clinical interpretation data such as number and severity of the pathologies identified in exams. Therefore, particular healthcare providers are not inappropriately credited or penalized, as part of determining quality scores 128, based on patient population dynamics. In this manner, grading algorithm 122 may be programmed to output provider quality scores 128, representing an overall quality score for a particular healthcare provider based on its error rate, the complexity of patients seen, and various features of the provider.

B. The quality scores 128 may be used in a designation process 130 to designate a particular healthcare provider using a particular label or designation from among a plurality of different labels or designations, using an ordered scale, hierarchical arrangement or other association of labels.

C. The quality scores 128 also may be provided to healthcare providers according to a structured communication process 132.

3. Overview of Estimating Diagnostic Error Rates Using Statistical Algorithms

Figure 2:
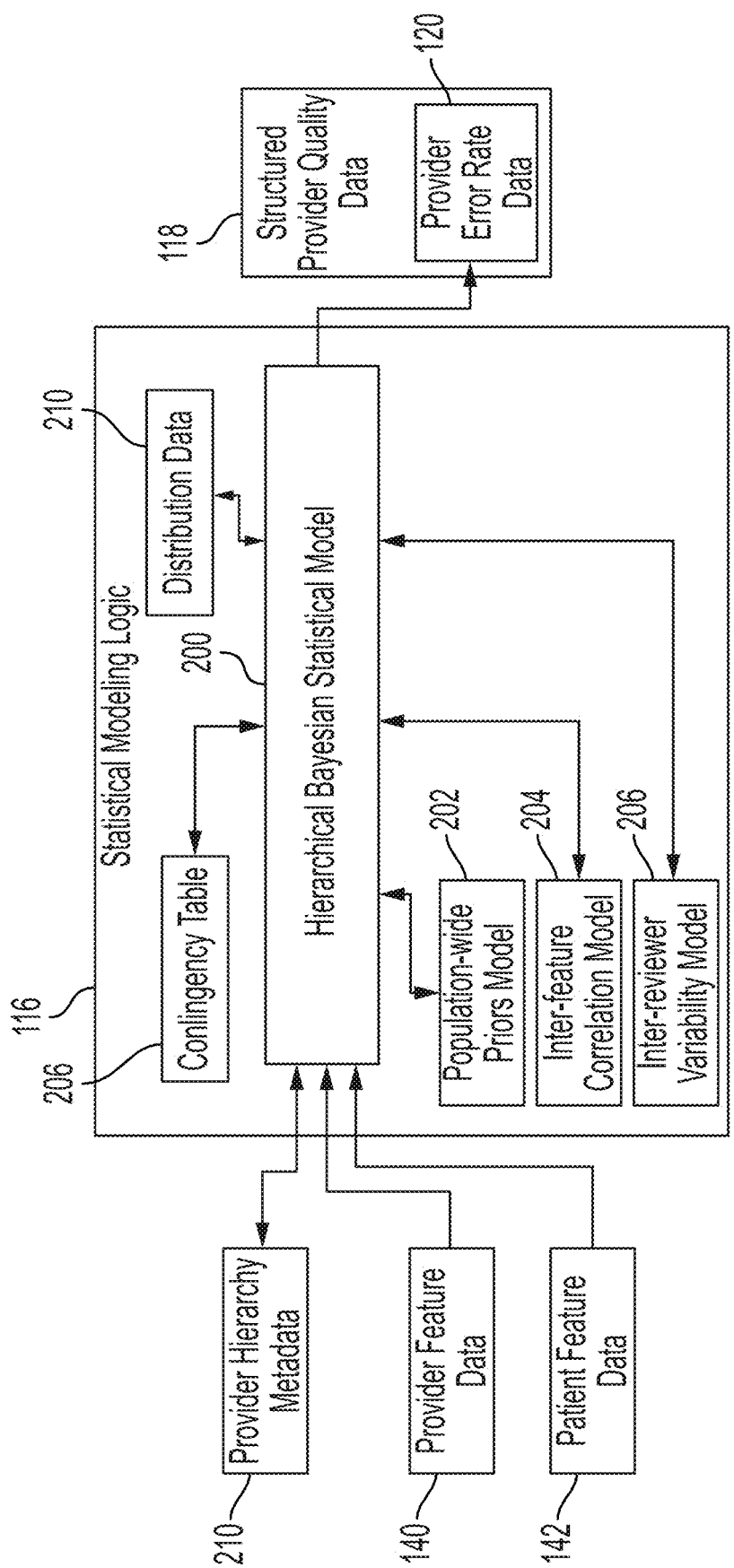
FIG. 2 illustrates further details of the statistical modeling logic of FIG. 1.
Figure 3:
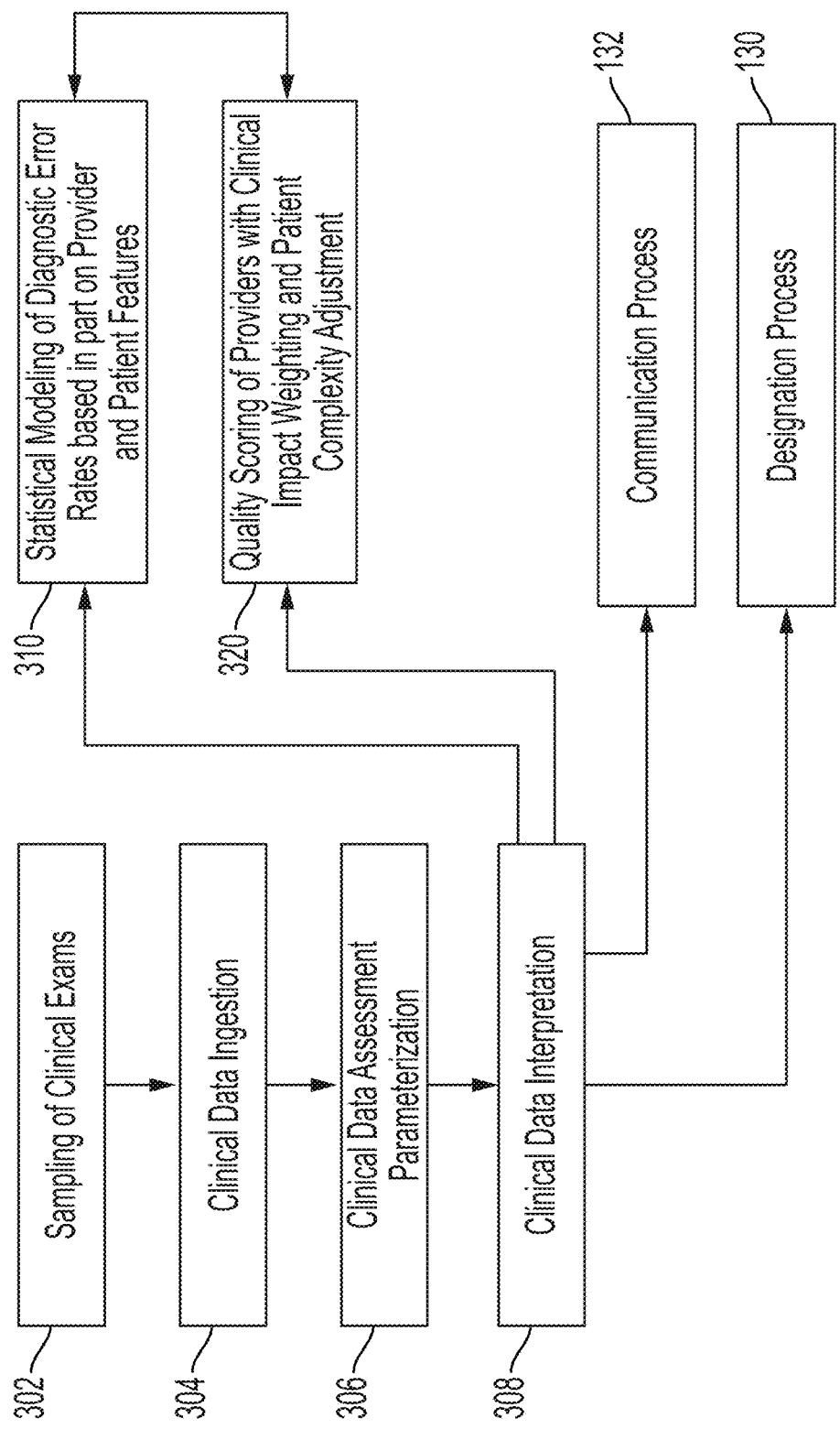
FIG. 3 illustrates an example data assessment process that may be used in an embodiment.

The system that has been generally described with reference to FIG. 1 may be used for estimating true diagnostic error rates via statistical algorithms. FIG. 2 illustrates further details of the statistical modeling logic of FIG. 1. FIG. 3 illustrates an example data assessment process that may be used in an embodiment. Referring first to FIG. 2, in one embodiment, the statistical modeling logic 116 is programmed to execute a hierarchical Bayesian statistical model 200. All elements of statistical modeling logic 116 are implemented using one or more computer programs, methods, web services, microservices and/or other software elements.

In an embodiment, foundation methodology for the statistical model 200 is to reduce outliers, narrow confidence intervals and improve the accuracy of estimates of true diagnostic error rates based on observed samples, especially for rarer types of diagnostic errors. In an embodiment, statistical model 200 uses a population-wide priors model 202, inter-feature correlation model 204 and inter-reviewer variability model 206. In an embodiment, the inter-reviewer variability model 206 is programmed to assess the reliability and consistency regarding the detection and measurement of specific types of diagnostic errors by reviewers. Its output may be used to assign confidence interval values and probability values to the provider error rate data 120 (FIG. 1). Statistical model 200 may store and use a contingency table 208 and distribution data 210 comprising one or more statistical distributions that are calculated as interim steps, as further described in this section.

In an embodiment, inter-feature correlation model 204 is programmed to use statistical techniques to characterize the correlation between groups of features. For example, groups of diagnostic error rates may be correlated; examples might be errors related to all lumbar spine pathologies, or the relationship between all diagnostic error rates of the type "overcall" to all diagnostic error rates of the type "undercall".

In an embodiment, the inter-reviewer variability model 206 is programmed to execute the seven-step process described above for parameterization logic 112, for a subset of exams consisting of associated digital images 104 and reports 105, for a plurality of different reviewers and to assess the level of agreement or disagreement of different reviewers, yielding an inter-reviewer variability score value. The inter-reviewer variability score value may be used as a factor in the statistical modeling logic 116.

In an embodiment, integration of provider feature data 140 and patient feature data 142 can further improve the estimate of true diagnostic error rates and can allow for estimates of diagnostic error rates for which the database 107 stores limited to no observed error rates. In the case of radiology, examples of features that can be represented in provider feature data 140 comprise educational history, size of practice and type of imaging equipment. Examples of features that can be represented in patient feature data 142 are age, sex, other demographic values and diagnosis.

Statistical model 200 also may receive provider hierarchy metadata 210, from database 107 for example. The provider hierarchy metadata 210 enables statistical model 200 to factor in the hierarchical structure of a healthcare provider. For example, provider hierarchy metadata 210 may specify that a particular provider is a practice, facility, individual physician or radiologist, or reflect other hierarchical levels or categories. In some embodiments, features of each entity represented in provider hierarchy metadata 210 include practice data such as size and academic affiliation; facility data such as type of imaging equipment and imaging protocols that are used; physician data such as years in practice and training attributes; and reviewer data such as years in practice and training attributes. Provider hierarchy metadata 210 may be created and stored for all the providers that are assessed using the computer system 10. The use of provider hierarchy metadata 210 enables statistical model 200 to differentiate and cross-relate features at the appropriate hierarchical level for each entity, thereby allowing for the most accurate estimate of true diagnostic error rates achieved by various practitioners.

In one embodiment, statistical model 200 is programmed to execute the following capabilities:

A. Estimation of the prevalence of diagnosis co-occurrence, via diagnosis co-occurrence statistical modeling.

B. Modeling of the agreement between reading provider and reviewer provider for a diagnosis at the item level, including: estimation of item-level diagnostic accuracy; calibration of the uncertainty of the "gold" standard diagnoses from reviewing providers using variability and inter-reviewer agreement measurements that are calculated from the data generated when multiple reviewing providers assess the same radiology exams and examples of the same pathologies and diagnostic errors.

C. Impact and significance mapping.

D. Item panel accuracy dependence.

E. Provider surveillance including modeling checklist levels and determining definitions of non-specific providers and adjustable providers.

F. Predictive extrapolation.

G. Information sharing and data pooling capabilities, including segmentation of provider populations, hierarchically informed estimation of population, and parsimonious inferential specifications.

In one embodiment, statistical model 200 is programmed to execute, using the computer system 10, functions that may be expressed for convenience in the following mathematical notation.

$$f\Big(R_{1l}, \ldots, R_{pl}, \tilde{R}_{1l}, \ldots, \tilde{R}_{pl}, D_{1l}, \ldots, D_{pl}, \theta_{1l}, \ldots,$$
$$\theta_{pl}, \mu, \sum_{\theta} | X^{(R)}, X^{(\tilde{R})}, X^{(D)}\Big) = f(R_{1l}, \ldots, R_{pl} | X^{(R)}) \times$$
$$\prod_{i=1}^{p} f(D_{il} | \tilde{R}_{il}, X^{(D)}, \theta_i) f(\tilde{R}_{il} | R_{il}, X^{(\tilde{R})}) f\Big(\theta_i | \mu, \sum_{\theta}\Big) \times f\Big(\mu, \sum_{\theta}\Big)$$

The expression above provides fully integrated probability characterizations of modeling specifications that are next described. Each component of the notation above represents a well-defined statistical estimation context. A Bayesian approach provides an optimized way to simultaneously address full uncertainty propagation and characterization at all data levels; incorporation of inherently unobserved measurements into the analysis; and flexible information pooling capabilities to permit identifying and representing the parsimonious dependency characteristics of the foundation data.

In an embodiment, the function $$f(R_{1l}, \ldots, R_{pl} | X^{(R)})$$

yields a log-linear contingency table represented in FIG. 2 as contingency table 208. The function provides a co-occurrence distribution of reviewing provider diagnoses $R_{1l}, \ldots R_{pl}$ for p items at location l with risk adjustment for features $X^{(R)}$.

In an embodiment, the function $$f(D_{il} | \tilde{R}_{il}, X^{(D)}, \theta_i) f(\tilde{R}_{il} | R_{il}, X^{(\tilde{R})})$$

provides a reading provider diagnosis distribution $D_{1l}$ for item I given uncertain true diagnosis $\sim R_{1l}$ given reviewing provider diagnosis $R_{1l}$. The component expression $$f((D_{il} | \tilde{R}_{il}, X^{(D)}, \theta_i)$$

represents a multi-class classification conditional on unobserved $\sim R_{1l}$. Performance of $D_{1l}$ relative to $R_{1l}$ provides item-level accuracy estimation, while integration over $\sim R_{1l}$ incorporates "gold standard" uncertainty into the model. Furthermore, the component expression $$f(\tilde{R}_{il} | R_{il}, X^{(\tilde{R})})$$

represents a categorical distribution capturing the observable variation in $R_{il}$. Observable variation in $\sim R_{il}$ is identified directly through repeated measures of multiple reviewing providers within specific checklists, as well as parametrically estimated across the population of all relevant checklists.

In an embodiment, an expert informed and healthcare impact driven score value may be derived by calculating:

$$g_k(R_{1l}, D_{1l}, \ldots, R_{pl}, D_{pl} | E_k, Y_k)$$

In which the function $g_k$ is defined on the basis of both expert opinion elicitation ($E_k$) and empirical evidence ($Y_k$) and aggregates accuracy portfolios into scores characterizing performance with respect to specific (k-th) financial and care outcomes.

In the expressions above, $\theta_i$ is a feature-driven, hierarchically informed parameter that is specific to $D_{1l} | \sim R_{1l}, X^{(D)}$. The structure and degree of dependence between $\theta_i$ (i=1, ... p), e.g., ($\theta_1, \ldots \theta_p$) approximates $f(\mu, \Sigma_\theta)$ explicitly models and drives accuracy dependency across item panels; the specification of this form addresses appropriateness and validation of the model.

In the expressions, $X^{(D)}$ may denote a provider or features characterizing providers, which allows for non-specific provider aggregations. Particular $\theta_i$ specifications reflect $X^{(D)}$ and capture associations attributable to $X^{(D)}$ while informing estimation across I via dependency structure in $\theta_i$.

Predictive extrapolation is available through standard $X^{(D)} \theta_i$ linear form inference.

Mixture model or post-hoc subpopulation segmentation provides aggregation driven estimation. Structure and dependency across $\theta_i$ provides hierarchical information pooling and sharing. Parsimonious feature engineering in log-linear model and multi-class classification contexts addresses infeasible saturated model approaches.

Mathematical notation has been used to describe embodiments herein for conciseness and convenience, and because it is the preferred language for communication between data scientists at the level of skill contemplated by this disclosure. However, nothing in this disclosure is intended to legally claim the use of mathematical functions or notations per se, in the abstract. Instead, the mathematical notation used herein is intended as a guide for skilled data scientists or others to program one or more computer programs to realize a practical application of the concepts that have been expressed. While numerous practical applications are described in other sections, in general, programs based on the mathematical notation herein may be applied to receive digital data representing physical anatomy or pathological reports, transform or classify the data, and generate output representing error rates and scores.

Referring now to FIG. 3, in one embodiment, the foregoing processes may be implemented using a feedback-oriented process starting at block 302 at which a sampling of clinical exams is performed. Block 302 may comprise executing the functions of sampling logic 106 (FIG. 1) that have been previously described, including all alternatives and variations.

At block 304, clinical data ingestion is performed. Block 304 may comprise executing the functions of clinical data ingestion logic 108 that have been previously described, including all alternatives and variations.

At block 306, clinical data assessment parameterization is performed. Block 306 may comprise executing the operations of structured assessment logic 110 as previously described, including all alternatives and variations.

At block 308, clinical data interpretation is performed. Block 308 may involve executing the operations of clinical data interpretation logic 114 as previously described, including all alternatives and variations.

At block 310, statistical modeling of diagnostic error rates based in part on provider features and patient features is performed. Block 310 may comprise executing the operations of statistical modeling logic 116 as previously described, including all alternatives and variations.

At block 320, quality scoring of providers with clinical impact weighting and patient complexity adjustment may be performed. Block 320 may comprise using structured provider quality data 118, including provider error rate data 120, with grading algorithm 122 and the weighting and patient complexity adjustment that have been described, to yield output provider quality scores 128, as previously described, including all alternatives and variations. Furthermore, the quality scores 128 may be provided as an element of feedback to block 310 to improve training and refinement of the statistical modeling logic 116.

4. Designation of Providers Based on Quality Scoring

In an embodiment, designation process 130 (FIG. 1) may be programmed, or used manually, to create and store designations of healthcare providers based on thresholds, a hierarchy or a ranking or labeling system. In one embodiment, radiology providers may be designated as high quality providers or Centers of Excellence based on the output provider quality scores 128 that are generated for the providers. Designations may be generated based on absolute values of the quality scores 128 or based on the scores in relation to later or downstream outcomes that are observed in patient populations. In some embodiments, data for outcomes for this purpose may be obtained from medical insurance claims records.

The designation process 130 may determine designations based on criteria such as comparison of quality scores 128 to thresholds derived from national benchmark data or regional benchmark data. The benchmark data may be stored in database 107 and may be determined over time by the computer system 10, by computing quality scores 128 for a plurality of providers and storing the score values in the database in association with provider identifying data that specifies geographic location. Thereafter, the score values may be sorted and grouped by region or nation to derive mean, median or other statistically significant values for providers in a particular group, region or nation. Then, a new quality score 128 generated for a particular provider can be compared to the benchmark for a region or nation in which that particular provider is located; if the new quality score passes a threshold value corresponding to the benchmark value, then a particular designation may be created and stored, or awarded.

These techniques are expected to permit assigning a designation with a high degree of statistical confidence. In some embodiments, the processes described in section (2) and section (3) of this document may be repeated on an ongoing basis to monitor the performance of providers over time, recalculate provider error rate data 120 and regenerate output provider quality scores 128 for the same providers. Ongoing repetition and recalculation in this manner is expected to further increase confidence levels associated with scores and designations.

5. Communication Processes

In some embodiments, communication process 132 (FIG. 1) may be programmed using presentation layer logic of computer system 10 to generate performance reports or dashboards that contain applications of the information generated via section (2) and section (3). The communication of provider error rate data 120, output provider quality scores 128, designations and/or data distilled from these values is expected to induce providers to elevate the standard of care that they provide.

6. Technical Benefits

Embodiments have been described that provide data-driven, objective assessment of healthcare provider diagnoses with the benefit of generating error data and quality scores that have not been available previously.

Typically, radiology or other healthcare quality measures are based on easily accessible proxy measures of medical care quality that focus on: process or workflow (e.g. average time between stroke patient arrival at provider facility and start of stroke treatment), structure (e.g. percentage of CT exam images and reports that providers make available to unaffiliated providers for the purposes of prior study comparisons), patient safety or outcomes (e.g. death rate of patients undergoing carotid artery stenting procedures), or subjective patient satisfaction surveys (e.g. patient feedback on wait times or physician bedside manner). These approaches to radiology quality measurement do not directly assess the quality of the medical care with respect to the accuracy of the imaging exams' diagnoses and rates of diagnostic errors.

The few examples of radiology or other quality measures that do focus directly on diagnostic accuracy and diagnostic errors, require a "gold standard" secondary medical test to be available for comparison, for example, the measure of mammography exam false positive rates that is defined by the Mammography Quality Standards Act (MQSA) of 1992 requires providers to compare positive mammography exams results to subsequent results of biopsy tests. This approach to quality measurement is not generalizable to most diagnostic imaging exams and exam types because secondary diagnostic tests are not routinely performed and available for comparison with the diagnostic imaging exam report.

Some formal peer review-based quality assessment programs have been proposed for use in radiology provider organizations, for example the American College of Radiology (ACR) has proposed the "RadPeer" program in which radiologists review a sample of radiology exams performed by other radiologists in their organizations and assign a subjective summary quality score of 1a, 2a, 2b, 3a, or 3b, to indicate if the overall quality of the diagnostic imaging exam under review achieved satisfactory or unsatisfactory quality and whether any diagnostic errors that are present are likely to have a clinically significant impact on the patient. This approach to quality measurement suffers from deficiencies that include: quality scores that do generalize across provider organizations, low levels of reproducibility, and quality scores that do not include any information on rates of specific types of diagnostic errors. These subjective peer review-based methods do not systematically capture information on the levels of inter-reviewer variability associated with specific aspects of the imaging exam quality assessments, and therefore: (1) are not able to appropriately weight attributes based on the confidence that specific diagnostic errors are present, or (2) supply appropriately confidence intervals around quality measures. Further, since peer reviewed methods like these only require the reviewing radiologist to assign a single summary quality score to each exam under review, and do not generate any granular or detailed information on specific types of diagnostic errors, they are not suitable for integration with computer-implemented machine learning methods.

Unlike existing radiology quality measurement systems, the embodiments described here produce radiology quality measures that: (1) are not proxy measures of clinical care quality and instead focus directly on the quality of diagnostic imaging care (i.e. diagnostic accuracy and rates of diagnostic errors), (2) do not require a secondary diagnostic test like a biopsy to be available to serve as a "gold standard comparison", and (3) are not based on subjective summary assessments from peers within the same provider organization and instead captures quality assessment data in a structured, granular and systematic manner that allows robust and reliable quantification of diagnostic error rates and associated confidence intervals.

Finally, the framework described here, in which structured data attributes related to diagnoses and diagnostic errors are generated from each exam quality assessment review, enables: (1) the method to be scaled and supplemented using machine-implemented algorithms that are trained using the reviewer-generated attributes, and (2) for correlations between the structured data attributes and additional provider attributes to be characterized, which allows measures of diagnostic error rates or weighted diagnostic error rates to be generate with improved accuracy and precision and generated for radiology providers which have not had any of their imaging exams subjected to standardized reviews (for whom only the supplementary data elements and attributes are available).

Consequently, the techniques herein provide opportunities for peer improvement by exposing objective and detailed factors that affect quality, rather than leaving medical disciplines to operate in an environment in which practices do not know why a particular practitioner has a high or low error rate, or may be associated with patients who experience better or worse healthcare outcomes. Instead, data features exposed in the present techniques provide reliable and robust measurements of error rates. This evidence can provide reasons to improve a practice's equipment, procedures, types of exam routing or other issues.

7. Machine Learning Network for Diagnostic Quality Assessment—General Overview

In some embodiments one or more machine learning algorithms can be trained to provide an automated assessment of the quality of a diagnostic made from a radiological exam—similar to the diagnostic assessment described above with respect to FIGS. 1-3. These machine learning algorithms (also referred to herein as "machine learning networks") can include, but are not limited to, neural networks, recurrent neural networks, convolutional neural networks, or one or more other machine learning algorithms more commonly referred to as deep learning algorithms. For example, a machine learning network trained according to the present disclosure receives as inputs the underlying radiological report and radiological images associated with a given diagnostic or patient, and then automatically regresses to an estimate of the error (if any) contained within the given diagnostic. Notably, the trained machine learning network performs this error regression calculation without requiring additional inputs or external guidance.

The following description refers to an exemplar scenario in which the underlying radiological exam (and hence the radiological reports and the radiological images provided to the disclosed machine learning networks) is a Lumbar Spine exam. Therefore, the discussion below refers to "motion segments," which are physiological units of the spine, each consisting of two adjacent vertebrae, the intervertebral disc and the adjoining ligaments between. Motion segments provide a nomenclature to identify and refer to various locations along the spine, and hence are particular to the example scenario of a lumbar spine exam. It is noted that this example is for illustrative purposes only and is not intended to be limiting as to the scope of the present application. The example of lumbar spine exams is provided to illustrate one specific application of the disclosed machine learning networks for automated diagnostic quality assessment—machine learning networks which, it is appreciated, can be applied to various types of different radiological exams, reports, and/or images without departing from the scope of the present disclosure.

8. Machine Learning Network For Diagnostic Quality Assessment—Architecture and Training Details The discussion turns next to FIGS. 4A-B, which depict a flowchart of a pre-processing pipeline 400 that receives as input raw radiological images 404 and radiological reports 405. In some embodiments, the radiological images 404 may be the same as the digital images 104 that are stored in the database described with respect to FIG. 1. Similarly, in some embodiments the radiological reports 405 may be the same as the physician diagnostic reports 105 that are also stored in the database described with respect to FIG. 1.

Pre-Processing Pipeline(s)

Figure 4B:
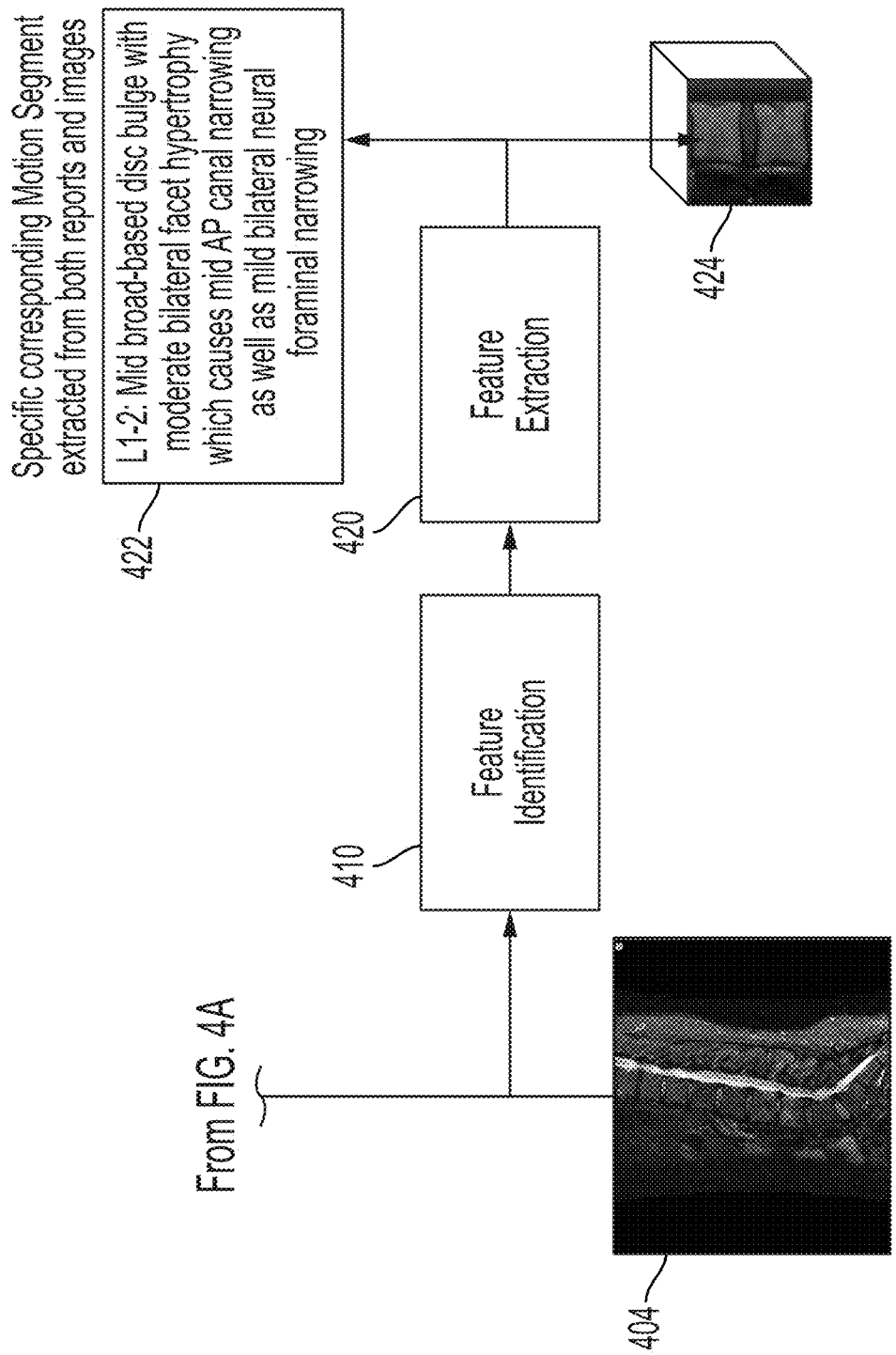

The discussion turns next to FIGS. 4A-B, which depict a flowchart of a pre-processing pipeline 400 that receives as input raw radiological images 404 and radiological reports 405. In some embodiments, the radiological images 404 may be the same as the digital images 104 that are stored in the database described with respect to FIG. 1. Similarly, in some embodiments the radiological reports 405 may be the same as the physician diagnostic reports 105 that are also stored in the database described with respect to FIG. 1.

Pre-processing pipeline 400 consists of a feature identification step 410 and a feature extraction step 420, which operate to clean and standardize the raw input radiological images 404 and radiological reports 405 into a format that is better and more effectively utilized by the down-stream machine learning networks depicted in FIGS. 5-8 (each of which will be discussed in turn below). Pre-processing pipeline 400 is designed to extract information to match anatomical sections from the radiological images and reports 404, 405. On the basis of this matching, the identified pairs or groups of anatomical sections identified from the radiological images and reports 404, 405 can thereafter be processed jointly. In the present example, in which the underlying radiological exam that produced the radiological images and reports 404, 405 is a lumbar spine exam, the anatomical sections upon which pre-processing pipeline 400 operates are motion segments (i.e., specific locations/vertebrae pairs along the spine).

Overall, the main purpose of this pre-processing step is to generalize the isolation of specific anatomical regions, as described in radiological reports, and to extract the corresponding regions in the medical images (e.g., MR/CT/Ultrasound/Digital Pathology, etc.) to match the assessment from both ends. Therefore, aspects of the present disclosure are applicable to any type of radiological and/or pathological exam, and the example application to spinal MRI images described below is not to be construed as limiting.

As illustrated, pre-processing pipeline 400 receives as input one or more sets of radiological images and reports 404, 405 that correspond to the same underlying patient/specific diagnostic. In some embodiments, these inputs might be received in substantially real-time, i.e. after the radiological report 404 is submitted by the examining radiologist, or after the radiological images 405 are retrieved from the scanner where they were captured. In some embodiments, one or more of the input radiological images and reports 404, 405 might be from a database or other storage system at some time after the original generation of the radiological image and/or report.

The input radiological images and reports 404, 405 are initially processed by independent pipelines. In other words, a first pre-processing pipeline is trained to perform feature identification 410 and feature extraction 420 with respect to input radiological reports 405, while a second pre-processing pipeline is trained to perform the same with respect to input radiological images 404.

For radiological reports 405, specific landmarks of interest (based on the actual exam) that might be extracted as features include the paragraphs or sentences within the report where the radiologist referred to or identified a particular motion segment. Text in the report referring to specific motion segments are isolated to be treated independently. For example, a sentence reading "L1-2: Mild broad-based disc bulge with moderate bilateral face hypertrophy which causes mild AP canal narrowing as well as mild bilateral neural foraminal narrowing" would be extracted as a motion segment feature for the L1-2 motion segment of the spine.

For radiological images 404, specific landmarks of interest that might be extracted as features include the image section or pixel area occupied by a particular motion segment. Because a single radiological exam might produce several different sequences of radiological images 404 (e.g. an MRI exam might produce a first sequence of T1w images, a second sequence of T2w images, etc.), the same given motion segment can be extracted multiple times, i.e. at least once for each constituent image sequence contained within the input radiological images 404. These multiple corresponding motion segments can then be treated independently, similar to the separate treatment of motion segments referred to in multiple places within the radiological report text.

In this manner, the application of pre-processing pipeline 400 to input data consisting of radiological images and reports provides structured output data pertaining to specific motion segments, i.e., in the form of corresponding image data 422 and text data 424 extracted from the radiological images and reports 404, 405, respectively. As depicted in FIG. 4, an example output of one pair/grouping of corresponding extracted data consists of: text section 422 (comprising a sentence reading "L1-2: Mild broad-based disc bulge with moderate bilateral face hypertrophy which causes mild AP canal narrowing as well as mild bilateral neural foraminal narrowing") and an image motion segment 424 (comprising the pixel area occupied by the L1-2 motion structure). Although not shown, it is appreciated that additional pairs/groupings of extracted data would also be generated for the full radiological report 405 and the full radiological image 404, e.g. for other identified motion segments such as L2-3, L3-4, etc.

In general, the pre-processing pipeline steps of feature identification 410 and feature extraction 420 are driven by the manner in which radiological assessments are performed by radiologists or other reviewing physicians using radiological images to generate diagnoses and/or radiological report, i.e., wherein anatomical regions are reviewed separately, one after the other. Accordingly, in some embodiments, pre-processing pipeline 400 identifies all of the motion segments that are present in the input radiological images 404 and extracts one or more image sections corresponding to each motion segment. Similarly, in some embodiments pre-processing pipeline 400 identifies all of the motion segments that are referred to or described in the input radiological reports 405 and extracts one or more text sections corresponding to each motion segment.

Multi-Regularizer Machine Learning Network for Diagnostic Error Detection

Figure 5:
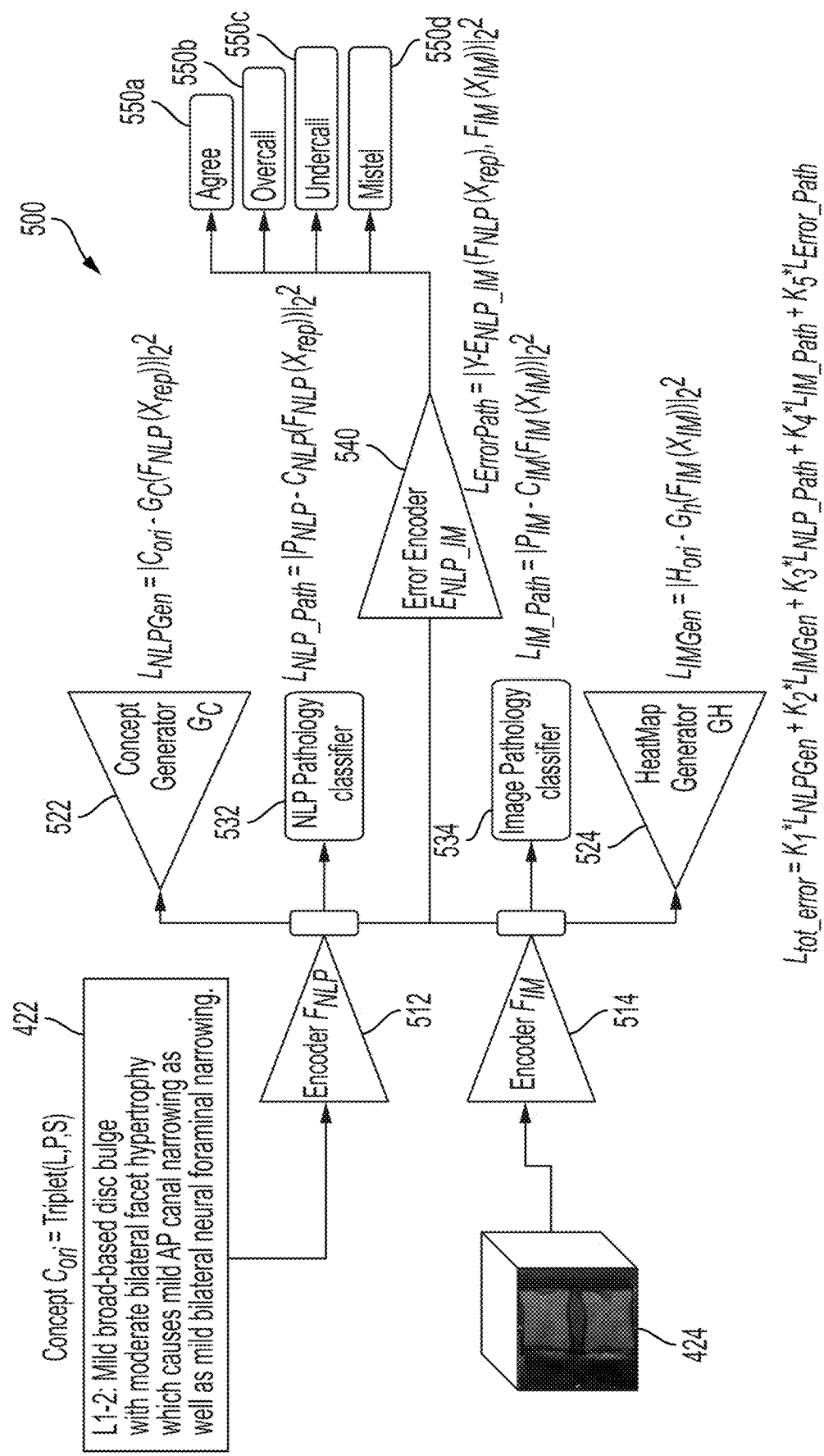
FIG. 5 illustrates an example architecture diagram for a multi-regularizer machine learning network to detect diagnostic errors in radiological examinations.

The disclosure turns now to FIG. 5, which depicts an architecture diagram for a multi-regularizer machine learning network 500 to detect diagnostic errors in radiological examinations. One or more portions, components, and/or layers of the machine learning network 500 (also referred to herein as the "ML network") can be provided as recurrent networks, non-recurrent networks, or some combination of the two, as will be described in greater depth below. Recurrent models can include, but are not limited to, recurrent neural networks (RNNs), gated recurrent units (GRUs), and long short-term memory (LSTMs). Additionally, one or more portions or components of the machine learning networks disclosed herein can be configured as fully-connected networks, convolutional neural networks (CNNs), or some combination of the two.

In operation, the trained ML network 500 receives as input a text section 422 (extracted from a full radiological report) and an image section 424 (extracted from a full radiological image) that both correspond to the same motion segment, pathology or anatomical location. In some embodiments, ML network 500 can receive the input text section 422 from the output of pre-processing pipeline 400 as applied to the full radiological report and can receive the input of image section 424 from the output of pre-processing pipeline 400 as applied to the full radiological image.

Without requiring additional inputs, the trained ML network 500 analyzes the text section 422 and the image section 424 against one another and generates an output indicating the quality of the diagnosis contained within text section 422. In particular, an output 550a denotes "Agree," or that the finding contained within text section 422 is generally in agreement or otherwise consistent with the pathologies contained within image section 424. An output 550b denotes "Overcall," or that the finding contained within text section 422 is more severe than the pathologies contained within image section 424 indicate. An output 550c denotes "Undercall," or that the finding contained within text section 422 is less severe than the pathologies contained within image section 424 indicate. Finally, an output 550d denotes "Missed," or that the finding contained within text section 422 is inconsistent with the pathologies contained within image section 424. The "Missed" output 550d can be further divided into false positives, in which the finding contained within text section 422 is absent from the pathologies contained within image section 424, and false negatives, in which a pathology contained within image section 424 is absent from the findings contained within text section 422. It is noted that the outputs 550a-d are provided for purposes of illustration, and that ML network 500 could be trained to provide a different set of outputs, providing more or less granularity as desired, without departing from the scope of the disclosure. For example, in some embodiments, the degree of Overcall and/or Undercall can also be included or otherwise represented in the regression. In this manner, greater granularity can be provided into the nature of Overcall and Undercall errors, e.g., the regression could introduce Overcall degree 1, 2, or 3 and Undercall degree 1, 2, or 3—although of course it is appreciated that various other granularity scales can be utilized without departing from the scope of the present disclosure. As will be explained in greater depth below, this is because the different outputs of ML network 500, such as the illustrated outputs 550a-d, are configured as the different categories or classes upon which an output classifier of ML network 500 is trained.

Although not depicted in FIG. 5, in some embodiments ML network 500 can additionally contain a second output classifier to regress to a clinical significance of the diagnostic error(s) 550b-c that are identified by the first output classifier described above. For example, the second output classifier could output a clinical significance score of 0, 1 or 2, where a score of 0 indicates no clinical significance (or no error), a score of 1 indicates a moderate clinical significance, and a score of 2 indicates a high clinical significance. However, it is appreciated that the exact outputs of a clinical significance classifier can be determined, modified or otherwise adjusted as desired during the training process of ML network 500. For example, the clinical significance scores can be a range of discrete numbers, as in the present example, or can be continuous between a minimum and maximum value. In some embodiments, the possible range of clinical significance scores might be determined by the definition of clinical significance provided by the overall quality assessment process in which the trained ML network 500 is utilized.

Advantageously, the trained ML network 500 does not require any additional inputs beyond the text sections 422 and the image sections 424—both of which are already collected and stored in the course of a conventional radiological exam. Similarly, a large portion of the training data needed to train ML network 500 and its constituent components can be obtained by leveraging the already existing data stored in, for example, database 107 of FIG. 1, which significantly reduces the burdensome need of actively collecting, collating and annotating training data from scratch. In some embodiments, additional or supplemental annotations can be generated and applied to the existing data obtained from databases such as database 107 of FIG. 1. For example, these additional/supplemental annotations could be utilized to specifically target pathologies within the images, or to replace missing annotations that otherwise would have already been associated with the existing data in database 107.

Recall that database 107 contains various forms of structured data generated from digital images 104 and reports 105—images and reports that are similar or even identical in form to the radiological images and reports 404, 405 upon which the trained ML network 1500 will be applied. For example, the structured data collected and stored in database 107 includes a plurality of checklists generated by parameterization logic 112, wherein a secondary physician reviewer (or one or more selected expert reviewers) views a radiological image and provides input indicating the presence, location, and extent of any pathologies present in the radiological image. The secondary physician reviewer/expert can furthermore view the initial report accompanying the same radiological image and provide input to the checklist of parameterization logic 112 indicative of any diagnostic errors contained within the initial report. As described previously, with respect to FIG. 1, database 107 contains a multiple thousands of these checklists and other structured data that parameterize the level of agreement or disagreement between the original physician/radiologist who produced the original report and one or more secondary physicians/selected experts who performed a review. Because the input images and reports used to generate the structured data and checklist reviews stored in database 107 are similar or identical to the radiological images 404 and radiological reports 405 that will be provided as inputs to the trained ML network 500, these checklist reviews can be utilized or transformed into annotated training data.

With respect to the machine learning architecture illustrated in FIG. 5, ML network 500 consists of three encoder networks, $F_{NLP}$, $F_{IM}$ and $E_{NLP\_IM}$, and at least one regularizer per encoder network. These regularizers contribute to the overall loss function that is used to train ML network 500, and more particularly, do so by defining specifically tailored losses to refine the encoder network to which the regularizer is attached. The training of ML network 500 is driven by categorical cross entropy loss, as will be explained in greater depth below.

First Encoder $F_{NLP}$, 512

The first encoder network 512, also referred to herein as $F_{NLP}$, is trained to generate embeddings for specific pathologies within the input section of report text 422. The input sections of report text 422 are provided to first encoder network 512 after being extracted from the overall radiological report 405 (i.e., using pre-processing pipeline 400 of FIG. 4). In some embodiments, the output of the radiological report pre-processing pipeline can be coupled to the input of first encoder network 512. However, it is also possible that the outputs from the radiological report pre-processing pipeline can be extracted in advance, then stored in a database and retrieved as needed by ML network 500 and first encoder 512. Regardless of how the input sections of report text 422 are obtained, first encoder 512 is trained to generate embeddings that represent pathologies in a consistent and more computationally advantageous manner. A word embedding is a real-valued vector that represents a single word based on the context in which it appears. By doing so, embeddings translate an input of many dimensions (e.g. the words within report text 422) into an output with a much smaller number of dimensions. In embodiments where the embeddings take the form of real-valued vectors within a pre-defined vector space, semantic information of the input report text 422 is in theory captured by the expectation that embeddings for semantically or syntactically related words will be closer to each other in the vector space than to unrelated words in the vector space. However, the degree to which the embeddings actually embody this relatedness is dependent on the text corpus or training data from which the first encoder network 512, $F_{NLP}$, learns to derive these embeddings.

In some embodiments, the first encoder network 512, $F_{NLP}$, can be of recurrent form. For example, $F_{NLP}$ might be provided as an Ordered Neuron Long Short-Term Memory (ON-LSTM) network, which have information (memory) retention characteristics that are particularly well suited for processing long input sequences such as report text 422. First encoder network 512 can also be a Transformer-based network, which is a deep learning model that is also designed to handle ordered sequences of data—such as report text 422—but without requiring that the input sequence be processed in order. In other words, a Transformer-based implementation of first encoder network 512 does not need to process the beginning of report text 422 before processing the middle or end of the text. Examples of Transformer-based machine learning networks include, but are not limited to, BERT (Bidirectional Encoder Representations from Transformers) and ClinicalBERT (a BERT model that has been pre-trained on a specialty corpus of clinical text and medical concepts).

Domain-specific training can be provided to first encoder network 512 to better refine $F_{NLP}$ for use in the radiological context in which both it and the overall ML network 500 are to be utilized. For example, a plurality of radiology reports can be assembled into a radiology-specific corpus of text, and first encoder network 512 can be obtained by training a dedicated Transformer model on the radiology-specific corpus. In some embodiments, first encoder network 512 can be pre-trained on a broader corpus, e.g., general English language, medical texts, clinical texts, etc., and then further trained on the radiology-specific corpus. It is noted that the radiology-specific corpus does not require annotation or manual labeling, as first encoder network 512 is able to learn word embeddings directly from the corpus in an unsupervised learning process. Accordingly, the radiology-specific corpus can be assembled from one or more of the radiology reports 105 that are stored in the database 107, as described with respect to FIG. 1, although it is also possible that the radiology-specific corpus be externally derived or obtained. In some embodiments, the word embeddings can be word2vec embeddings, although it is appreciated that various other types of embeddings can be utilized without departing from the scope of the present disclosure.

As mentioned previously, each encoder network within ML network 500 is associated with at least one regularizer. With respect to the first encoder 512, $F_{NLP}$, the architecture diagram of FIG. 5 depicts two associated regularizers: a concept generator 522 (labeled as $G_C$) and an NLP pathology classifier 532 ($C_{NLP}$). By defining an additional loss component that is incorporated into the overall loss function used to train ML network 500, each of the two regularizer networks specifically targets and refines the manner in which first encoder 512 learns or generates word embeddings for the sections of report text 422.

The first regularization network consists of concept generator 522, $G_C$, which trains and refines the manner in which the first encoder 512, $F_{NLP}$, syntactically parses and analyzes the report text 422. Report text 422 contains diagnosis information that reflects the reviewing physician or radiologist's interpretation of the medical image data 424. This diagnosis information typically consists of a location, a pathology, and a severity—although other constituent components can be used to form the diagnosis information without departing from the scope of the present disclosure. However, there are often numerous different ways (in terms of syntax, grammar, word choice, etc.) in which a reviewing physician or radiologist might choose to express what is otherwise the exact same diagnosis information. Accordingly, concept generator 522 helps standardize the handling and treatment of non-standardized natural language textual inputs such as report text 422.

As indicated in FIG. 5, original diagnosis information can be represented by a 'concept' data structure $C_{ori}$, which is a triplet given by (L, P, S), where L is the location of the identified pathology, P is the identified pathology, and S is the severity of the identified pathology. Concept generator 522 helps regularize first encoder 512 by applying a training process in which the encoding features of $F_{NLP}$ are used to generate synthetic data (new concept triplets) that are matched against known information of a corresponding type or form (the original concept triplet $C_{ori}$). On this basis, concept generator 522 can be used to drive a loss $L_{NLPGen}$ that minimizes the difference between the generated new concept triplet and the original concept triplet $C_{ori}$.

Concept generator 522 can be trained to output new concept triplets for inputs of actual report text 422. In such a scenario, the requisite annotated training data can consist of labeled pairs of report text and the corresponding original concept triplet $C_{ori}$ for that report text. Notably, rather than having to annotate an immense amount of radiological report text by hand, the pre-existing radiological reports and structured data stored within database 107 of FIG. 1 can be leveraged to automatically generate the requisite training data in the form of data pairs comprising {radiological report text, corresponding original concept triplet $C_{ori}$}.

In some embodiments, rather than using original concept triplets $C_{ori}$, concept generator 522 can instead, or additionally, be trained to output relevant sections of text that relate to the actual report text input. In other words, concept generator 522 can be trained to identify relevant regions or sets of words within an input report text 422 for each of the three diagnostic attributes of the concept triplets, i.e. location, pathology, severity. In this scenario, concept generator 522 refines first encoder 512 by applying category saliency to highlight the area/regions of report text that are discriminative for the three different diagnostic attributes.

Regardless of which output type concept generator 522 is configured to produce, concept generator 522 constitutes an additional component used to fine-tune the training of first encoder 512 and the remainder of machine learning network 500. Based on the loss function $L_{NLPGen}$, the loss of concept generator 522 is back propagated to refine the various layers and parameters of first encoder 512, $F_{NLP}$.

The second regularization network that is applied to first encoder 512, $F_{NLP}$ consists of an NLP pathology classifier 532 ($C_{NLP}$). NLP pathology classifier 532 trains and refines first encoder 512 with respect to the independent pathology classification for input report text 422. Any given segment of input report text 422 has an associated ground truth, which in this case can be thought of as the diagnosis as the reviewing physician/radiologist intended to read the radiological images. Where the first regularization network (i.e., concept generator 522) was directed more toward refining structural and/or efficiency aspects of the manner in which first encoder 512 analyzes and processes input report text 422, the second regularization network (i.e., NLP pathology classifier 532) is directed more toward refining the accuracy of the conclusions that first encoder 512 outputs based on its analysis of the input report text 422—the automated diagnostic quality evaluation performed by machine learning network 500 depends upon a correct interpretation of the radiological report that is the subject of the evaluation.

NLP pathology classifier 532 consists of classification layers added off of embeddings from the first encoder network 512, $F_{NLP}$. In some embodiments, these classification layers are driven by a binary cross entropy (BCE) loss $L_{NLP\_Path}$. BCE loss is utilized here because the output pathology classification for a segment of input report text 422 is either correct (i.e., the same as the ground truth pathology for report text 422) or incorrect (i.e., not the same as the ground truth pathology for report text 422). By minimizing the BCE loss $L_{NLP\_Path}$, the first encoder network 512 is regularized and refined with respect to its ability to detect pathologies from input report text 422 relative to the ground truth. The requisite training data used in conjunction with NLP pathology classifier 532 can be obtained in much the same way as was described previously with respect to the training data for concept generator 522—by leveraging pre-existing radiological reports and structured clinical interpretation data stored, for example, in database 107 of FIG. 1. Because these radiological reports 105 have already been interpreted by, e.g., clinical data interpretation logic 114, training data for use with NLP pathology classifier 532 can be generated by annotating a given report 105 with the one or more pathologies determined by clinical data interpretation logic 114, as these pathologies are the ground truth for the given report 105.

Second Encoder $F_{IM}$, 514

The disclosure turns now to second encoder network 514, also referred to herein as $F_{IM}$. Broadly, what $F_{NLP}$ performs for segments of input report text 422, $F_{IM}$ performs for segments of input radiological image regions 424.

Second encoder network 514 is trained to generate features (or embeddings) from the set of imaging sequences available for specific anatomical regions. The input radiological image regions 424 are provided to second encoder network 514 after being extracted from the overall radiological images 404 (i.e., using pre-processing pipeline 400 of FIG. 4). In some embodiments, the output of the radiological image pre-processing pipeline can be coupled to the input of second encoder network 514, although it is also possible that the outputs from the radiological image pre-processing pipeline can be extracted in advance, then stored in a database and retrieved as needed by ML network 500 and second encoder network 514.

In some embodiments, second encoder network 514 can be based on ResNet (a type of residual neural network) or DenseNet (a dense convolutional network), with a proper adaptation to medical images that handles anisotropy and the diverse intensity distribution that are associated with and typical in many of the radiological images that are provided as input to second encoder network 514.

Just as first encoder network 512 is regularized by a generator network (522) and a pathology classifier (532), so too is second encoder network 514. In particular, as illustrated, second encoder network 514 is regularized by a heatmap generator network 524 and an image pathology classifier 534.

Heatmap generator 524, $G_H$, refines the manner in which second encoder 514, $F_{IM}$ analyzes the input images 424. Heatmap generator 524 is trained such that second encoder 514 is fine-tuned to focus on certain image locations or anatomical regions that have been observed or are otherwise known to be relevant to pathological structures. In this manner, second encoder 514 is trained to, in effect, give greater weight to relevant portions of input images 424 (e.g. portions that include anatomical and/or pathological structures) and lesser weight to non-relevant portions of the input images (e.g. the empty space surrounding the anatomical/pathological structures, such as the black space on the left and right sides of the example input image 424 shown in FIG. 5). Second encoder 514 is therefore trained away from outputting features based on portions of radiological images that a reviewing physician/radiologist would not consider when performing their review. For example, assuming that input image 424 contains one or more pathologies of interest, then these pathologies will usually be located in specific portions of the input image, e.g., a bulged disc will be located between or near two vertebrae In some embodiments, heatmap generator 524 can be configured to generate attention heatmaps from specific layers of second encoder 514. These attention heatmaps, or activation maps, represent the discriminative image regions used by second encoder 514 in identifying a specific feature in an input image 424. As noted above, knowledge of the relevant portions of a radiological image for making a diagnosis or identifying pathological structure(s) can be used to create annotated heatmaps, which serve as training data for heatmap generator 524. In some embodiments, one or more annotated heatmaps can be automatically generated by tracking gaze information of a radiologist as he or she reviews radiological images, with heatmap intensity reflecting the amount of time that the radiologist focused on a given location of the radiological image.

Heatmap generator 524 can be trained through a process that provides training data pairs comprising {sample input image, annotated heatmap for the sample input image}. The sample input image is fed through second encoder 514, and heatmap generator 524 generates one or more heatmaps corresponding to layers of the second encoder as they processed the sample input image. By defining a loss function $L_{IMGen}$ to minimize the difference between the heatmaps generated by heatmap generator 524 and the annotated heatmap from the training data pair, second encoder 514 is refined such that its discriminative regions become better aligned with the known relevant regions of radiological images.

In some embodiments, second encoder 514 can be regularized via a decoder that performs specific segmentation of anatomical structures and/or pathological structures from an input image. Similar to the description above regarding the generated heatmaps vs. annotated heatmaps, the segmentation decoder can be trained on annotated segmentation data, such that loss $L_{IMGen}$ between the decoder's segmentation of a training data input image and the annotated segmentation of the same training data input image is minimized. In this manner, the second encoder 514, $F_{IM}$ is refined to optimize its output features such that the segmentation of input images 424 is optimized as well.

Image pathology classifier 534, also labeled in FIG. 5 as $C_{IM}$, provides a further layer of regularization to second encoder 514 (much in the same manner to how NLP pathology classifier 532 regularizes the first encoder 512). For example, image pathology classifier 534 trains and refines second encoder 514, $F_{IM}$ with respect to the independent pathology classification for input images. In this scenario, the independent pathology classification for input images 424 can be thought of as the diagnosis/pathology identification as is actually contained within the input images 424 (i.e. the ground-truth pathology, independent of what the original reviewing physician or radiologist reported that he saw in the same input image 424).

Image pathology classifier 534 consists of classification layers added off of features from the second encoder network 514, $F_{IM}$. In some embodiments, these classification layers can be driven by a binary cross entropy (BCE) loss $L_{IM\_Path}$, which for a given input image 424, captures the difference between the ground truth pathology in the input image and the pathology in the features generated by second encoder 514. BCE loss is utilized because the second encoder 514 is either correct or incorrect with respect to the ground truth pathology of any given input image, although in some embodiments a non-binary loss could be used to capture pathology classification errors with greater granularity. Regardless of whether a binary loss is utilized or not, by training ML network 500 while also minimizing $L_{IM\_Path}$, second encoder 514 is regularized and refined with respect to its ability to detect pathologies from input images 424.

The requisite training data that can be used in conjunction with image pathology classifier 534 can be obtained as annotated radiological images (or annotated sections of radiological images), where the annotations reflect one or more expert opinions (and/or an expert consensus) as to the pathologies that are present in a given radiological image. In some embodiments, this annotated radiological image pathology training data can be obtained from the expert review previously described with respect to FIGS. 1 and 2, wherein an expert or secondary reviewing physician analyzes a given radiological image and provides user input corresponding to structured checklist items that pertain to various pathologies. In particular, these structured checklists can be stored in database 107 and associated with the radiological image from which the structured checklist was generated. In some embodiments, the pairs of structured checklists and corresponding radiological images can be processed and use to generate training data in response to the structured checklist and corresponding radiological image initially being written to or stored in database 107. It is also possible that a plurality of structured checklists and their corresponding radiological images be retrieved from database 107 at a later time and then processed into one or more training data sets (and/or validation sets, test sets, etc.).

$F_{NLP\_IM}$=Error Encoder 540

As illustrated in FIG. 5, first encoder 512, $F_{NLP}$ receives as input radiological report text 422 and outputs one or more embeddings for pathologies and/or diagnosis information within the report text. Second encoder 514, $F_{IM}$ receives as input radiological image regions 424 (corresponding to report text 422) and outputs one or more features for pathologies within the image. The embeddings from first encoder 512 and the features from second encoder 514 are concatenated to an error encoder 540, $E_{NLP\_IM}$ which is trained to regress to an estimation of diagnostic error by classifying a {word embedding, image feature} pair across the output categories 550a-d (Agree, Overcall, Undercall, Missed).

Figure 7:
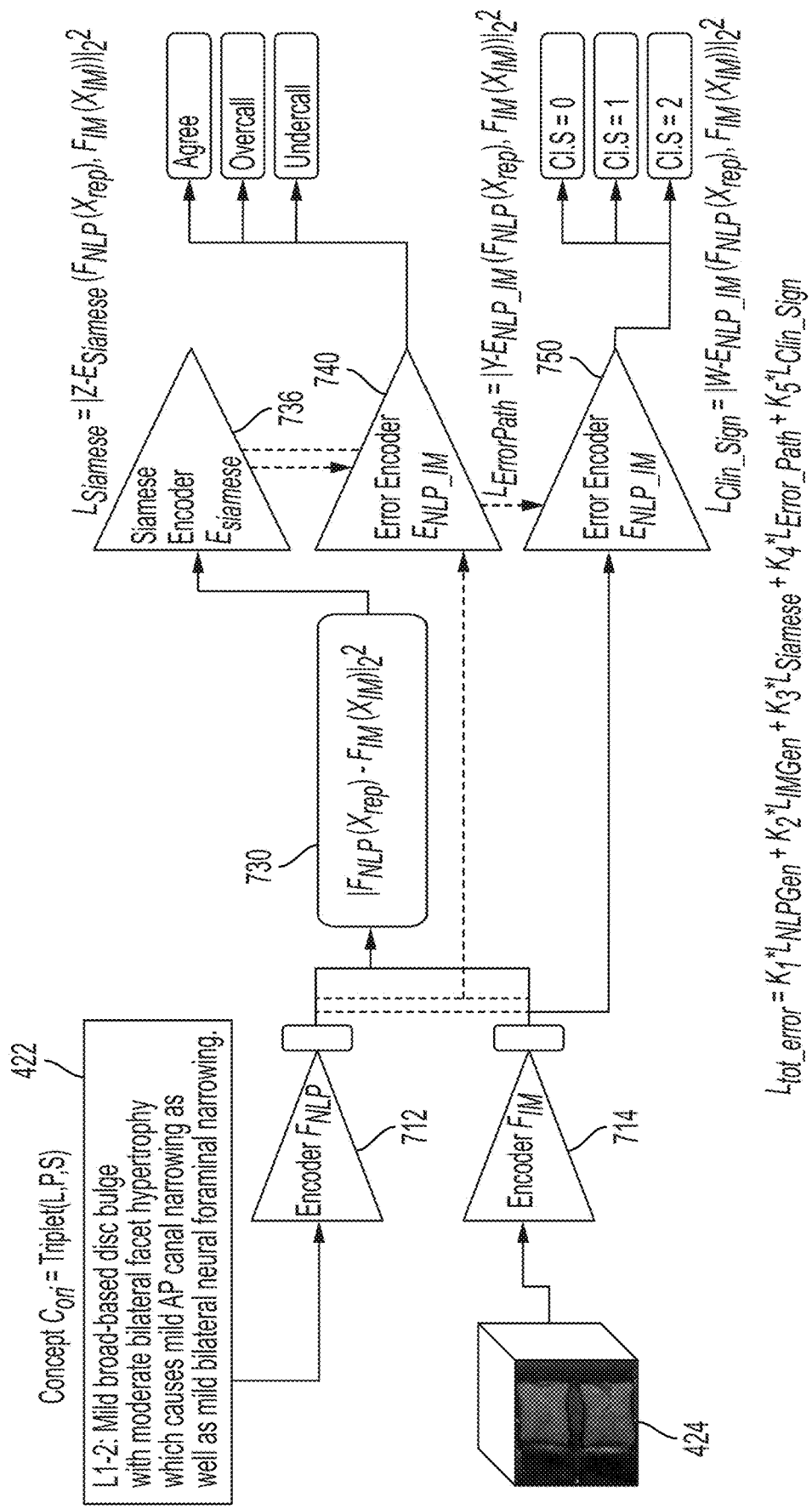
FIG. 7 illustrates an example architecture diagram for a Siamese-like machine learning network that is extended to regress to an estimated clinical significance of error in addition to an estimation of diagnostic error.

In some embodiments, ML network 500 can include an additional encoder network (not shown) that is used as a second task or classifier to regress to an estimation of the clinical significance of a diagnostic error classified by error encoder 540. (An example of one such clinical significance encoder $E_{Clin\_Sig}$ 750 is depicted in FIG. 7 and is discussed in greater depth with respect to FIG. 7). For example, the output categories 550b-d (Overcall, Undercall, Missed) all indicate that a diagnostic error of some sort is present. For each identified diagnostic error from the error encoder 540, the clinical significance encoder could output a clinical significance score of 0, 1 or 2, where a score of 0 indicates no clinical significance (or no error), a score of 1 indicates a moderate clinical significance, and a score of 2 indicates a high clinical significance. However, it is appreciated that the exact outputs of a clinical significance classifier can be determined, modified or otherwise adjusted as desired during the training process of ML network 500. For example, the clinical significance scores can be a range of discrete numbers or can be continuous between a minimum and maximum value. In some embodiments, the possible range of clinical significance scores might be determined by the definition of clinical significance provided by the overall quality assessment process in which the trained ML network 500 is utilized.

Error encoder 540 is trained on the basis of a loss $L_{Error\_Path}$, which is used to minimize the difference between a ground truth diagnostic error, Y, and the output diagnostic error generated by error encoder 540. As depicted in FIG. 5, the output diagnostic error generated by error encoder 540 is given by the function $E_{NLP\_IM}(F_{NLP}(X_{rep}), F_{IM}(X_{IM}))$, where $X_{rep}$ represents the input report text 422 and $X_{IM}$ represents the input image 424—$F_{NLP}(X_{rep})$ represents the word embedding(s) output by first encoder 512 for input report text 422 and $F_{IM}(X_{IM})$ represents the image feature(s) output by second encoder 514 for input image 424.

In this manner, error encoder 540 is trained, driven by the loss $L_{Error\_Path}$, to regress to an estimation of diagnostic error, where the estimation is given by one of the output categories 550a-d. Training data for error encoder 540 is based upon annotated input training data pairs comprising radiological report text (such as report text 422) and radiological images (such as images 424), where the annotation of relevance uses the output categories 550a-d to label any diagnostic error(s) present in the training data pair. These annotations or labels indicative of diagnostic error (and, if using a clinical significance encoder, also indicative of the clinical significance [0, 1, 2] of each diagnostic error) can be obtained from the structured checklists and other structured data stored in database 107 of FIG. 1, for example.

In this scenario, the ground truth presence of diagnostic error can be determined by presenting one or more checklist items to the reviewing physician(s) and/or expert(s) that use the checklists to review radiological reports and images. For example, checklist items might directly receive user input indicating a diagnostic error falling within one of the output categories 550a-d. The checklist items might also receive user input pertaining to the pathologies present in a radiological image and corresponding report, in which case annotations or labels for the training data can be automatically generated by determining the appropriate output category 550a-d based on a structured checklist for the radiological image and a checklist for the corresponding report. Similarly, in some embodiments a structured checklist item can be used to obtain user input indicating a degree of clinical significance for a given diagnostic error in a radiological image/report pair. A clinical significance checklist item can be presented in line with the aforementioned checklist items, or can be presented at a later time, e.g. in a separate fashion where secondary reviewing physicians/experts are asked only to indicate a clinical significance for already identified diagnostic errors.

In some embodiments, the checklist items and/or user input can include comments about image quality, i.e., a checklist item is a request for comments about the image quality of the particular radiological image with which the checklist is associated. Based on these comments, ML network 500 can assess the quality of the radiological image (e.g., presence of artifacts such as motion and/or blur, noise, bad acquisition protocol, etc.) to determine whether or not the image is acceptable enough for further assessment by downstream portions of ML network 500. The user input of comments reflecting image quality can be provided as a single checklist item allowing for relatively free form entry and identification of artifacts, or the user input can be provided as a comprehensive set of checklist items, e.g., one checklist item for each type of artifact that may or may not be present in the radiological image being reviewed with the checklist. Moreover, by correlating radiological image quality with an observed error rate, a corresponding feature vector of this network can be added to ML network 500, wherein the features can be reviewed by one or more controllers contained within ML network 500.

Accordingly, the overall ML network 500 is trained end-to-end, not to classify the presence or absence of pathologies, but rather to regress to an estimation of the diagnostic errors made in the assessment of radiological images by the reviewing physician. In some embodiments, the five different losses discussed above are aggregated into a final total loss function that is used to train the overall ML network 500, e.g. with the aggregate loss function given by $L_{tot\_error} = k_1 * L_{NLPGen} + k_2 * L_{IMGen} + k_3 * L_{NLP\_Path} + k_4 * L_{IM\_Path} + k_5 * L_{Error\_Path}$.

In the equation above, $k_i$ for i=1 ... 5 corresponds to particular weight(s) applied to each individual loss. The $k_i$ weighting factors can be set empirically, can be grid searched for optimization, or some combination of the two can be applied. In this manner, the application of the aggregate loss function $L_{tot\_error}$ simultaneously trains ML network 500 to regress to an estimation of diagnostic error, while also regularizing and refining the various individual components such as $F_{NLP}$ (first encoder 512), $F_{IM}$ (second encoder 514), and $E_{NLP\_IM}$ (error encoder 540).

With respect to training of the overall ML network 500, training data generation can leverage already existing radiological images 104 and radiological reports 105 that are stored within database 107 of FIG. 1. Moreover, the training data generation can leverage various structured data and structured checklists that contain user input provided by secondary reviewers/experts, to thereby generate and apply annotations and labels to raw training data pairs comprising radiological images 104 and their corresponding radiological reports 105. In this manner, ML network 500 and its associated training can be provided to be backwards compatible with pre-existing radiological practices and databases, providing automated diagnostic quality assessments in a powerful and integrated fashion.

Siamese-Like Machine Learning Network for Diagnostic Error Detection

In some embodiments, a limited amount of training data (i.e. radiological images and their corresponding radiological reports) might be available, or it may otherwise be impractical to obtain such images and reports in the requisite large volumes. Therefore, in some embodiments the automated diagnostic quality assessment of the present disclosure can utilize a Siamese-like network, which are functional even when a limited number of training data are available.

Figure 6A:
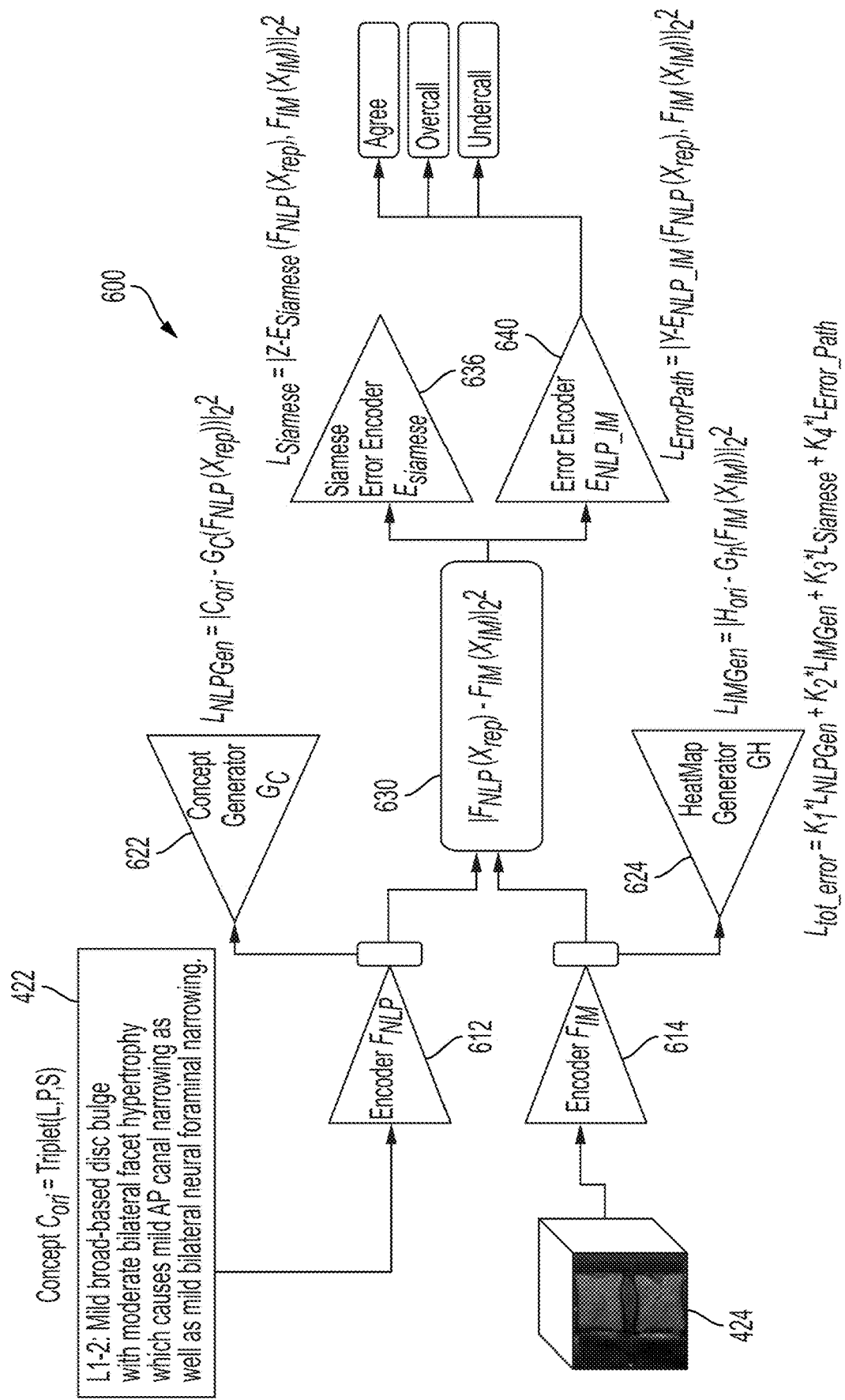
FIG. 6A illustrates an example architecture diagram for a Siamese-like machine learning network to detect diagnostic errors in radiological examinations.

The disclosure turns now to FIG. 6A, which depicts an architecture diagram for Siamese-based machine learning network 600 to detect diagnostic errors in radiological examinations. As illustrated, the Siamese ML network 600 shares architectural similarities with the multi-regularizer ML network 500 of FIG. 5. For example, Siamese ML network 600 includes a first encoder network 612 ($F_{NLP}$) and a second encoder network 614 ($F_{IM}$)—in some embodiments, the first and second encoder networks 612, 614 can be substantially similar or identical to the first and second encoder networks 512, 514 of multi-regularizer ML network 500. Additionally, Siamese ML network 600 includes a concept generator 622 ($G_C$) and a heatmap generator 624 ($G_H$), which in some embodiments can be substantially similar or identical to the concept generator 522 and heatmap generator 524 of multi-regularizer ML network 500.

As compared to FIG. 5, Siamese ML network 600 replaces pathology classifiers (i.e. NLP pathology classifier 532 and image pathology classifier 534) with a Siamese network 630. Instead of performing a classification, a Siamese network optimizes the differences between input objects $X_1$, $X_2$ that are either of a similar class or different classes, using an $-h(X_1)-h(X_2)|$ norm to drive the loss of the network. In the particular case of Siamese network 630, the input objects are the radiological report text embeddings output by first encoder $F_{NLP}$ 612 and the radiological image features output by second encoder $F_{IM}$ 614. In other words, Siamese network 630 operates over the {text embedding, image feature} pairs generated for each motion segment within an overall diagnostic examination of a patient. The particular Siamese function of Siamese network 630 takes the form $|F_{NLP}(X_{rep})-F_{IM}(X_{IM})|$, where $X_{rep}$ once again represents the input report text 422 and $X_{IM}$ represents the input image 424.

In training, a Siamese Error Encoder $E_{Siamese}$ 636 drives a Siamese loss $L_{Siamese}$ for input training data consisting of {text embedding, image feature} pairs. The training data is structured such that each training data pair is either of a similar class (i.e., same pathology present in both) or is of a different class (i.e., same pathology is not present in both). The degree to which a training data pair agrees or disagrees is indicated by an annotation/label 'Z', which can be a binary or continuous variable depending on the manner or extent in which discrepancies are to be encoded. The Siamese loss $L_{Siamese}$ minimizes the difference between the label Z (representing the ground truth) and the calculated Siamese difference between the text embedding and the image feature (which is output by Siamese function 630).

When the training data inputs are of the same class, the Siamese loss $L_{Siamese}$ forces the {text embedding, image feature} pair to be similar, or to have a very small distance between each other. Conversely, when the training data inputs are not of the same class (i.e., the diagnostic from report text 422 has notable differences from the diagnostic from images 424), the Siamese loss $L_{Siamese}$ tries to separate the two as much as possible, or to increase their separation distance. In this manner, the outputs of first encoder $F_{NLP}$ 612 and second encoder FIM 614 are refined—their embeddings and features are fine-tuned such that they may be better analyzed and classified for the automated assessment of diagnostic quality and error disclosed herein. A second encoder, labeled here as Error Encoder $E_{NPL\_IM}$ 640 regresses to the actual error value for the input pair of report text 422 and radiological image 424, in the same or similar manner as described above with respect to error encoder 540 of FIG. 5, and provides the output indicating diagnostic quality (e.g., Agree, Overcall, Undercall, Missed).

As illustrated, four different losses are aggregated into a final total loss function that is used to train the overall Siamese ML network 600, e.g. with the aggregate loss function given by $L_{tot\_error} = k_1 * L_{NLPGen} + k_2 * L_{IMGen} + k_3 * L_{Siameseh} + k_4 * L_{Error\_Path}$. In the aggregate loss function, $k_i$ for i=1 . . . 4 corresponds to particular weight(s) applied to each individual loss. The $k_i$ weighting factors can be set empirically, can be grid searched for optimization, or some combination of the two can be applied. In this manner, the application of the aggregate loss function $L_{tot\_error}$ trains Siamese ML network 600 to regress to an estimation of diagnostic error.

In FIG. 6A, the regression to diagnostic error is computed off of the Siamese function 630. However, in some embodiments, regression to the estimation of diagnostic error can be computed off of $F_{NLP}$ (first encoder 612) and $F_{IM}$ (second encoder 614), for example as is shown in FIG. 6B.

Figure 6B:
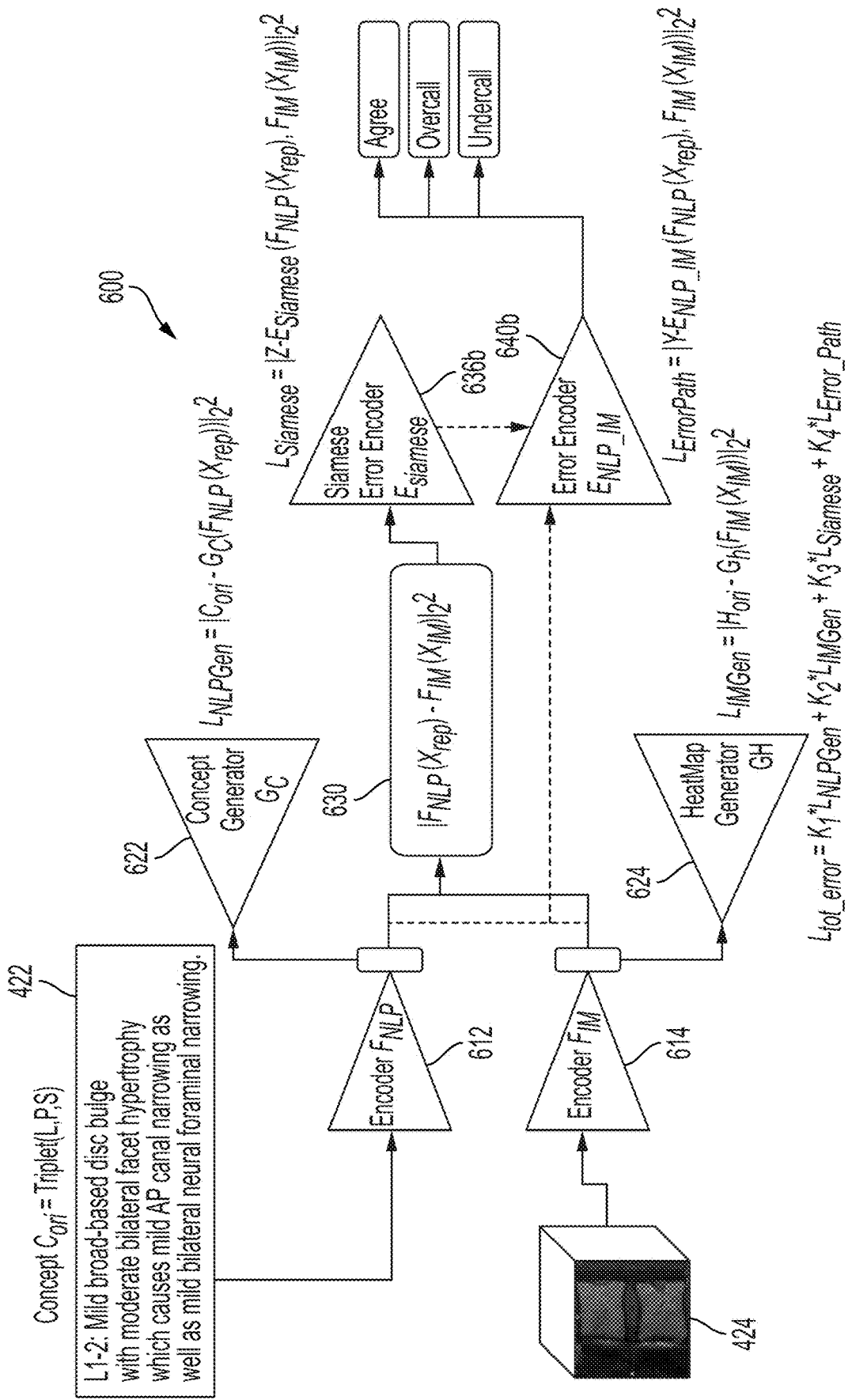
FIG. 6B illustrates an example architecture diagram for an additional Siamese-like machine learning network to detect diagnostic errors in radiological examinations.

The Siamese function 630 is still present in the architecture of FIG. 6B, but no longer couples to error encoder 640b. Instead, error encoder 640b couples to $F_{NLP}$ and $F_{IM}$ and receives their respective outputs of text embeddings and image features. During training, the Siamese function 630 and the Siamese loss $L_{Simese}$ nevertheless still influence $F_{NLP}$ and $F_{IM}$ at back propagation, to refine the two encoders based on the Siamese network principles discussed above. Additionally, Siamese Error Encoder $E_{Simese}$ 636b is configured as a controller to error encoder 640b. Thus, given a Siamese distance between text and image features, error encoder 640b regresses to the actual diagnostic error output (Agree, Overcall, Undercall, Missed) and in some embodiments, the clinical significance of error (0, 1, 2) as well.

FIG. 7 depicts a Siamese ML network 700 that has been extended to regress to an estimated clinical significance of error in addition to the estimation of diagnostic error discussed above. As illustrated, Siamese ML network 700 adds a clinical significance encoder $E_{Clin\_Sig}$ 750 to the multitask network architecture of FIG. 6B, although it is appreciated that the clinical significance encoder 750 could be combined with or added to any of the previously discussed machine learning architectures for automated diagnostic quality assessment without departing from the scope of the present disclosure.

In some embodiments, clinical significance encoder $E_{Clin\_Sig}$ 750 is provided as a final regressor with a sigmoid activation function for the clinical significance score. For example, the clinical activation score(s) can be obtained from database 107, and in particular, obtained as generated by the clinical impact weighting logic 320 discussed previously with respect to FIG. 3. The clinical significance score may alternatively or additionally be obtained as a user input to one or more structured checklists, as described above with respect to ML network 500 of FIG. 5.

Clinical significance encoder $E_{Clin\_Sig}$ 750 takes into account the Siamese input from Siamese error encoder $E_{Siamese}$ 736 as well as the embeddings/features input obtained from first encoder $F_{NLP}$ 712 and second encoder $F_{IM}$ 714. In some embodiments, the Siamese input from $E_{Siamese}$ can be utilized as a regularizer for the weight of clinical significance encoder $E_{Clin\_Sig}$ 750 and/or can be added to the features generated by $E_{Clin\_Sig}$. The features from error encoder $E_{NLP\_IM}$ 740 can be aggregated to clinical significance encoder $E_{Clin\_Sig}$ 750 in a similar fashion. A clinical significance loss $L_{Clin\_Sig}$ is added to the total loss function $L_{tot\_error}$. $L_{Clin\_Sig}$ is used to minimize the difference between a ground truth clinical significance for the diagnostic error present in a training data pair and the computer clinical significance output by clinical significance encoder $E_{Clin\_Sig}$ 750 for that same training data pair.

In some embodiments, one or more clinical references such as patient age, weight, history (e.g., of previous related pathologies) can be added to any of the machine learning networks and architectures discussed above, e.g., added as a feature vector to be used in the automated diagnostic quality assessment or provided as a feature matrix. Such a feature vector can be utilized at the image-based assessment section of the machine learning pipeline, to ensure that the clinical information is appropriately utilized. For example, the feature vector can be passed as a controller (e.g., a Clinical Controller) and concatenated with the features from $F_{IM}$, which is the imaging encoder network (represented variously as encoder 514, 614, 714 in the discussion above).

9. Machine Learning Network for Diagnostic Quality Assessment—Input Features to a Bayesian Approach One or more of the components of the aforementioned machine learning networks discussed with respect to FIGS. 5-7 can be configured to additionally calculate and output uncertainties along with its predictions. For example, first encoder $F_{NLP}$ (512), second encoder $F_{IM}$ (514), and/or error encoder $E_{NLP\_IM}$ (540) of ML network 500 could output an uncertainty along with their respective prediction outputs. Methods for determining these uncertainties can include, but are not limited to, evidential deep learning and stochastic weight averaged gaussian approaches. In some embodiments, the uncertainty associated with the one or more model parameters is assessed and provided as an additional model output, rather than performing a separate or subsequent calculation in order to obtain the uncertainties. The output form can express the uncertainty in a raw number, such as a percentage, or as a feature vector, for example. Feature vectors generated by the three models (i.e., $F_{NLP}$, $F_{IM}$, and $E_{NLP\_IM}$) can be utilized by additional downstream components, systems, or networks associated with or otherwise coupled to ML network 500. In some embodiments, a threshold (or set of thresholds) can be individually set for each one of the three models $F_{NLP}$, $F_{IM}$, and $E_{NPL\_IM}$ such that a confidence level can be determined with each output prediction. Such confidence levels can be used, for example, to define one or more specific workflows, as will be described in greater depth below. Examples of such workflows can include, but are not limited to, rerouting uncertain cases for further or expert assessment, selecting specific examples for model fine-tuning (e.g., the generation of augmented training data or other parameter adjustments), and to improve the assessment of physicians' accuracies in delivering their diagnoses.

Physicians' diagnostic accuracies are quantified based on review data, which may be produced by one or more human experts (i.e., as described previously with respect to FIGS. 1-3) and/or which may be produced by one or more machine learning networks or AI models, as is described below. For example, review data can be obtained from a computer vision machine learning model, such as second encoder $F_{IM}$(514) of FIG. 5 and/or can be obtained from a natural language processing model, such as first encoder $F_{NLP}$ (512) of FIG. 5. Regardless of its source, it is contemplated that review data capture deterministically or probabilistically the accuracy of the diagnosis that the original reviewing physician made, e.g., in other words, was the diagnosis correct or incorrect, and if incorrect, what type (and/or degree) of error was made? The following example and discussion can utilize one or more of the following form fields as predictors for modeling physicians' diagnostic accuracies:

Physician npi
Practice label
Patient age group (22-55, etc.)
Study body part (Lumbar, etc.)
Field name (Central Canal Stenosis, etc.)
Pathology (Moderate, etc.)

Each physician's diagnostic accuracy is estimated for each combination of study body part, field name, and pathology that is present in the set of review data. In some embodiments, it is assumed that the diagnostic accuracies of the physicians belonging to the same practice are correlated. Furthermore, it is assumed that the patient age group affects the diagnostic accuracy of each combination of study body part, field name, and pathology. It is appreciated that one or more (or all) of the above-mentioned form fields can be automatically generated from or by ML network 500 and its constituent encoders $F_{NLP}$, $F_{IM}$, $E_{NLP\_IM}$ and/or its other constituent systems and components, as previously described above with respect to FIGS. 5-7.

The description below provides for the use of one or more feature vectors and/or form fields automatically generated from one or more outputs of ML networks 500-700 in providing feature inputs to a Bayesian approach to estimate physicians' accuracies in diagnosing a pathology. In particular, an approach using deterministic review data and an approach using probabilistic review data will be described. The following notation will be employed in describing both the deterministic and the probabilistic Bayesian approaches:

N-simplex is defined as $\Delta^N = \{(p_1, p_2, \ldots, p_N) | \Sigma_{i=1}^N p_i = 1$ and phd $i>0$ $\forall i:1'i \leq N\}$.

the number of physicians is denoted as $N_{physicians}$
the number of practices is denoted as $N_{practices}$
the number of reviews is denoted as $N_{reviews}$
the number of age groups is denoted as $N_{age\ groups}$
the number of body parts is denoted as $N_{body\ parts}$
the number of field names is denoted as $N_{field\ names}$
the number of pathologies is denoted as $N_{pathologies}$ Additionally, each piece of review data (i.e., produced by one or more of ML networks 500-70 for pairs of radiological images and the corresponding report text written by the physician reviewing the radiological images) has several associations.

Each ML review i is associated with:
a physician (physician: $\{1, 2, \ldots, N_{reviews}\} \rightarrow \{1, 2, \ldots, N_{physician}\}$)
an age group of the patient (age: $\{1, 2, \ldots, N_{reviews}\} \rightarrow \{1, 2, \ldots, N_{age\ groups}\}$)
a body part of the study (bp: $\{1, 2, \ldots, N_{reviews}\} \rightarrow \{1, 2, \ldots, N_{body\ parts}\}$)
a field name (field names: $\{1, 2, \ldots, N_{reviews}\} \rightarrow \{1, 2, \ldots, N_{field\ names}\}$)
a pathology (path: $\{1, 2, \ldots, N_{reviews}\} \rightarrow \{1, 2, \ldots, N_{pathologies}\}$)

Each physician is associated with a practice:
practice: $\{1, 2, \ldots, N_{physicians}\} \rightarrow \{1, 2, \ldots, N_{practices}\}$ As mentioned above, the Bayesian approaches described herein estimate physicians' diagnostic accuracy for each unique combination of body parts, field names, and pathologies that are present in the study (i.e., in some embodiments, the set of ML review data i). Each unique concept is represented as a triplet. The number of these triplets is denoted as $N_{body\ parts, field\ names, pathologies}$. Moreover, each ML review i is further associated with one of these triplets:
bp_fn_path: $\{1, 2, \ldots, N_{reviews}\} \rightarrow \{1, 2, \ldots, N_{body\ parts, field\ names, pathologies}\}$ Bayesian Approach using Deterministic Reviews Under a Bayesian approach using deterministic review data, deterministic review data (produced by an ML network/AI, or by expert human reviewer(s)) are of the form:
$y_i \in \{$agree, missed finding, overcall, undercall, false positive$\}$ where i=1, 2, ..., $N_{reviews}$. In other words, each review represented in the deterministic review data is classified according to one of the labels/categories above.

A generative hierarchical model is formulated for the deterministic review data as follows:

$\beta_l^{bp\_fn\_path} \sim N(0, 2^2 I)$
where l=1, 2, ..., $N_{body\ parts, field\ names, pathologies}$
$\beta_{m,l}^{age, bp\_fn\_path} \sim N(0, I)$
where m=1, 2, ..., $N_{age\ groups}$ and l=1, 2, ..., $N_{body\ parts, field\ names, pathologies}$
$\beta_{j,l}^{practice, bp\_fn\_path} \sim N(0, I)$
where j=1, 2, ..., $N_{practice}$ and l=1, 2, ..., $N_{bodyparts, field\ names, pathologies}$
$\sigma^2 \sim \Gamma^{-1}(3, 1)$
$\beta_{k,i}^{physician, bp\_fn\_path} \sim N(\beta_{practice(j),i}^{practice, bp\_fn\_path}, \sigma^2 I)$
where k=1, 2, ..., $N_{physicians}$ and l=1, 2, ..., $N_{body\ parts, field\ names, pathologies}$
$\gamma_i = \beta_{bp\_fn\_path(i)}^{bp\_fn\_path} + \beta_{age(i), bp\_fn\_path(i)}^{age, bp\_fn\_path} + \beta_{physician(i), bp\_fn\_path(i)}^{physician, bp\_fn\_path}$
where i=1, 2, ..., $N_{reviews}$
$p_i = \text{Softmax}((\gamma_i^T, 0)^T$
where i=1, 2, ..., $N_{reviews}$
$y_i \sim \text{Categorical}(p_i)$
where i=1, 2 ..., $N_{reviews}$ and where:
$\beta_l^{bp\_fn\_path}, \beta_{m,l}^{age, bp\_fn\_path}, \beta_{j,l}^{practice, bp\_fn\_path}, \beta_{k,i}^{practice, bp\_fn\_path}, \beta_{k,i}^{physician, bp\_fn\_path}, \gamma_i \in \mathbb{R}^4$, $\sigma^2 \in \mathbb{R}_{>0}$, and $p_i \in \Delta^5$.

Figure 9:
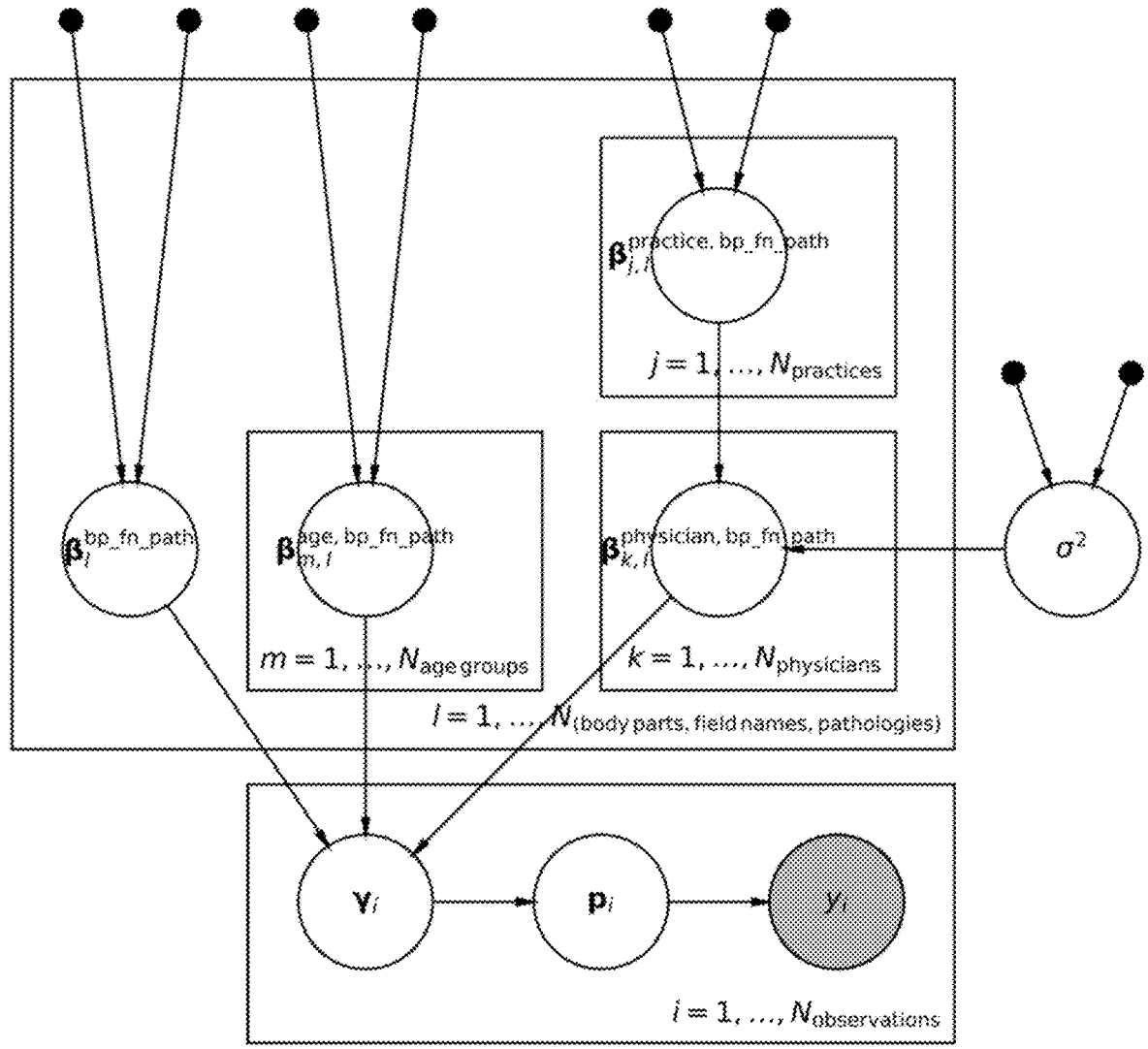
FIG. 9 illustrates a plate notation for a Bayesian approach to radiology quality scoring with AI and/or human QA data.

FIG. 9 depicts a plate notation for the generative hierarchical model described above. White (unshaded) circles represent latent variables, while gray (shaded) circles represent observed variables. The circular black points represent fixed parameters provided as inputs. The directed edges between the fixed parameters and the variables represent dependencies. The plates represent variable repetitions.

In some embodiments, the model described above and depicted in FIG. 9 is conditioned on observed data. The posterior distribution of the latent variables (e.g., one or more of $\beta_l^{bp\_fn\_path}$, $\beta_{m,l}^{age,bp\_fn\_path}$, $\beta_{j,l}^{practice,bp\_fn\_path}$, $\sigma^2$, $\beta_{k,l}^{physician,bp\_fn\_path}$, $\gamma_i$, $p_i$) is then estimated in order to quantify the certainty about the variables.

For example, analysis of $\beta_{m,l}^{age,bp\_fn\_path}$ allows for the quantification of the effect of patient age on diagnostic accuracy across body part, field name, and pathology combinations. Similarly, by analyzing $\beta_{k,l}^{practice,bp\_fn\_path}$, the effect of a physician's practice or practice group on diagnostic accuracy can be quantified across body part, field name, and pathology combinations. Likewise, an analysis of $\beta_{k,l}^{physician,bp\_fn\_path}$ can quantify diagnostic accuracies of individual physicians across body part, field name, and pathology combinations.

Bayesian Approach using Probabilistic Reviews

Under a Bayesian approach using probabilistic review data, probabilistic review data (produced by an ML network such as networks 500-700, an AI, and/or one or more expert human reviewers) are given by the form:

$$y_i = \begin{pmatrix} \alpha_i^{agree} \\ \alpha_i^{missed\ finding} \\ \alpha_i^{overcall} \\ \alpha_i^{undercall} \\ \alpha_i^{false\ positive} \end{pmatrix} \in \mathbb{R}^5,$$

where i=1, 2, . . . , $N_{reviews}$.

In some embodiments, the vectors $y_i$ (also referred to herein as feature vectors) are treated as parameters defining Dirichlet distributions over probabilities of agree, missed finding, overcall, undercall, and false positive.

A hierarchical model is formulated for the probabilistic review data as follows:

$\beta_l^{bp\_fn\_path} \sim N(0, 2^2 I)$
 where l=1, 2, . . . , $N_{body\ parts, field\ names, pathologies}$
$\beta_{m,l}^{age,bp\_fn\_path} \sim N(0,I)$
 where m=1, 2, . . . , $N_{age\ groups}$ and l=1, 2, . . . , $N_{body\ parts, field\ names, pathologies}$
$\beta_{j,l}^{practice,bp\_fn\_path} \sim N(0,I)$
 where j=1, 2, . . . , $N_{practice}$ and l=1, 2, . . . , $N_{bodyparts, field\ names, pathologies}$
$\sigma^2 \sim \Gamma^{-1}(3,1)$
$\beta_{k,l}^{physician,bp\_fn\_path} \sim N(\beta_{practice(j),l}^{practice,bp\_fn\_path}, \sigma^2 I)$
 where k=1, 2, . . . , $N_{physicians}$ and l=1, 2, . . . , $N_{body\ parts, field\ names, pathologies}$
$\gamma_i = \beta_{bp\_fn\_path(i)}^{bp\_fn\_path} + \beta_{age(i),bp\_fn\_path(i)}^{age,bp\_fn\_path} + \beta_{physician(i),bp\_fn\_path(i)}^{physician,bp\_fn\_path}$
 where i=1, 2, . . . , $N_{reviews}$
$p_i = \text{Softmax}((\gamma_i^T, 0)^T$ where i=1, 2, . . . , $N_{reviews}$
$p_i \sim \text{Dirichlet}(y_i)$, where i=1, 2 . . . , $N_{reviews}$
and where:
$\beta_l^{bp\_fn\_path}, \beta_{m,l}^{age,bp\_fn\_path}, \beta_{j,l}^{practice,bp\_fn\_path}, \beta_{k,l}^{practice,bp\_fn\_path}, \beta_{k,l}^{physician,bp\_fn\_path}, \gamma_i \in \mathbb{R}^4$, $\sigma^2 \in \mathbb{R}_{>0}$, and $p_i \in \Delta^5$.

In some embodiments, the probabilistic model described above is conditioned on the probabilistic review data $y_i$, i=1, 2, . . . $N_{reviews}$. The distributions of the latent variables are estimated in order to quantify the certainty about the variables. For example, analysis of $\beta_{m,l}^{age,bp\_fn\_path}$ allows for the quantification of the effect of patient age on diagnostic accuracy across body part, field name, and pathology combinations. Similarly, by analyzing $\beta_{k,l}^{practice,bp\_fn\_path}$, the effect of a physician's practice or practice group on diagnostic accuracy can be quantified across body part, field name, and pathology combinations. Likewise, an analysis of $\beta_{k,l}^{physician,bp\_fn\_path}$ can quantify diagnostic accuracies of individual physicians across body part, field name, and pathology combinations.

10. Implementation Example—Computer System

According to one embodiment, the techniques described herein are implemented by at least one computing device. The techniques may be implemented in whole or in part using a combination of at least one server computer and/or other computing devices that are coupled using a network, such as a packet data network. The computing devices may be hard-wired to perform the techniques, or may include digital electronic devices such as at least one application-specific integrated circuit (ASIC) or field programmable gate array (FPGA) that is persistently programmed to perform the techniques, or may include at least one general purpose hardware processor programmed to perform the techniques pursuant to program instructions in firmware, memory, other storage, or a combination. Such computing devices may also combine custom hard-wired logic, ASICs, or FPGAs with custom programming to accomplish the described techniques. The computing devices may be server computers, workstations, personal computers, portable computer systems, handheld devices, mobile computing devices, wearable devices, body mounted or implantable devices, smartphones, smart appliances, internetworking devices, autonomous or semi-autonomous devices such as robots or unmanned ground or aerial vehicles, any other electronic device that incorporates hard-wired and/or program logic to implement the described techniques, one or more virtual computing machines or instances in a data center, and/or a network of server computers and/or personal computers.

Figure 8:
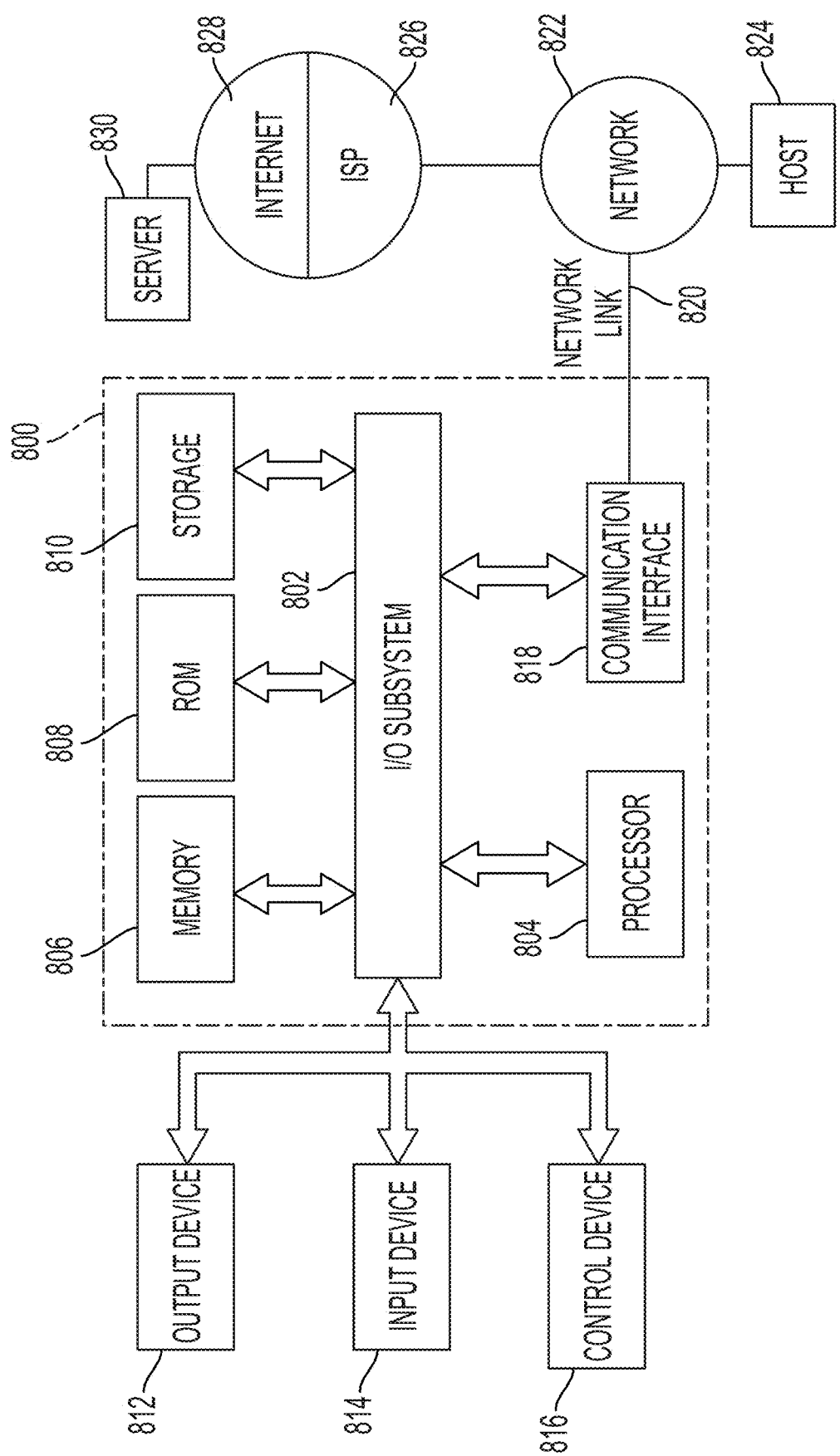
FIG. 8 illustrates an example computer system, with non-transitory computer-readable storage media, that may be used to implement all or part of one or more aspects of the present disclosure.

FIG. 8 is a block diagram that illustrates an example computer system with which an embodiment may be implemented. In the example of FIG. 8, a computer system 800 and instructions for implementing the disclosed technologies in hardware, software, or a combination of hardware and software, are represented schematically, for example as boxes and circles, at the same level of detail that is commonly used by persons of ordinary skill in the art to which this disclosure pertains for communicating about computer architecture and computer systems implementations.

Computer system 800 includes an input/output (I/O) subsystem 802 which may include a bus and/or other communication mechanism(s) for communicating information and/or instructions between the components of the computer system 800 over electronic signal paths. The I/O subsystem 802 may include an I/O controller, a memory controller and at least one I/O port. The electronic signal paths are represented schematically in the drawings, for example as lines, unidirectional arrows, or bidirectional arrows.

At least one hardware processor 804 is coupled to I/O subsystem 802 for processing information and instructions. Hardware processor 804 may include, for example, a general-purpose microprocessor or microcontroller and/or a special-purpose microprocessor such as an embedded system or a graphics processing unit (GPU) or a digital signal processor or ARM processor. Processor 804 may comprise an integrated arithmetic logic unit (ALU) or may be coupled to a separate ALU.

Computer system 800 includes one or more units of memory 806, such as a main memory, which is coupled to I/O subsystem 802 for electronically digitally storing data and instructions to be executed by processor 804. Memory 806 may include volatile memory such as various forms of random-access memory (RAM) or other dynamic storage device. Memory 806 also may be used for storing temporary variables or other intermediate information during execution of instructions to be executed by processor 804. Such instructions, when stored in non-transitory computer-readable storage media accessible to processor 804, can render computer system 800 into a special-purpose machine that is customized to perform the operations specified in the instructions.

Computer system 800 further includes non-volatile memory such as read only memory (ROM) 808 or other static storage device coupled to I/O subsystem 802 for storing information and instructions for processor 804. The ROM 808 may include various forms of programmable ROM (PROM) such as erasable PROM (EPROM) or electrically erasable PROM (EEPROM). A unit of persistent storage 810 may include various forms of non-volatile RAM (NVRAM), such as FLASH memory, or solid-state storage, magnetic disk or optical disk such as CD-ROM or DVD-ROM and may be coupled to I/O subsystem 802 for storing information and instructions. Storage 810 is an example of a non-transitory computer-readable medium that may be used to store instructions and data which when executed by the processor 804 cause performing computer-implemented methods to execute the techniques herein.

The instructions in memory 806, ROM 808 or storage 810 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. The instructions may implement a web server, web application server or web client. The instructions may be organized as a presentation layer, application layer and data storage layer such as a relational database system using structured query language (SQL) or no SQL, an object store, a graph database, a flat file system or other data storage.

Computer system 800 may be coupled via I/O subsystem 802 to at least one output device 812. In one embodiment, output device 812 is a digital computer display. Examples of a display that may be used in various embodiments include a touch screen display or a light-emitting diode (LED) display or a liquid crystal display (LCD) or an e-paper display. Computer system 800 may include other type(s) of output devices 812, alternatively or in addition to a display device. Examples of other output devices 812 include printers, ticket printers, plotters, projectors, sound cards or video cards, speakers, buzzers or piezoelectric devices or other audible devices, lamps or LED or LCD indicators, haptic devices, actuators or servos.

At least one input device 814 is coupled to I/O subsystem 802 for communicating signals, data, command selections or gestures to processor 804. Examples of input devices 814 include touch screens, microphones, still and video digital cameras, alphanumeric and other keys, keypads, keyboards, graphics tablets, image scanners, joysticks, clocks, switches, buttons, dials, slides, and/or various types of sensors such as force sensors, motion sensors, heat sensors, accelerometers, gyroscopes, and inertial measurement unit (IMU) sensors and/or various types of transceivers such as wireless, such as cellular or Wi-Fi, radio frequency (RF) or infrared (IR) transceivers and Global Positioning System (GPS) transceivers.

Another type of input device is a control device 816, which may perform cursor control or other automated control functions such as navigation in a graphical interface on a display screen, alternatively or in addition to input functions. Control device 816 may be a touchpad, a mouse, a trackball, or cursor direction keys for communicating direction information and command selections to processor 804 and for controlling cursor movement on display 812. The input device may have at least two degrees of freedom in two axes, a first axis (e.g., x) and a second axis (e.g., y), that allows the device to specify positions in a plane. Another type of input device is a wired, wireless, or optical control device such as a joystick, wand, console, steering wheel, pedal, gearshift mechanism or other type of control device. An input device 814 may include a combination of multiple different input devices, such as a video camera and a depth sensor.

In another embodiment, computer system 800 may comprise an internet of things (IoT) device in which one or more of the output device 812, input device 814, and control device 816 are omitted. Or, in such an embodiment, the input device 814 may comprise one or more cameras, motion detectors, thermometers, microphones, seismic detectors, other sensors or detectors, measurement devices or encoders and the output device 812 may comprise a special-purpose display such as a single-line LED or LCD display, one or more indicators, a display panel, a meter, a valve, a solenoid, an actuator or a servo.

When computer system 800 is a mobile computing device, input device 814 may comprise a global positioning system (GPS) receiver coupled to a GPS module that is capable of triangulating to a plurality of GPS satellites, determining and generating geo-location or position data such as latitude-longitude values for a geophysical location of the computer system 800. Output device 812 may include hardware, software, firmware and interfaces for generating position reporting packets, notifications, pulse or heartbeat signals, or other recurring data transmissions that specify a position of the computer system 800, alone or in combination with other application-specific data, directed toward host 824 or server 830.

Computer system 800 may implement the techniques described herein using customized hard-wired logic, at least one ASIC or FPGA, firmware and/or program instructions or logic which when loaded and used or executed in combination with the computer system causes or programs the computer system to operate as a special-purpose machine. According to one embodiment, the techniques herein are performed by computer system 800 in response to processor 804 executing at least one sequence of at least one instruction contained in main memory 806. Such instructions may be read into main memory 806 from another storage medium, such as storage 810. Execution of the sequences of instructions contained in main memory 806 causes processor 804 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage 810. Volatile media includes dynamic memory, such as memory 806. Common forms of storage media include, for example, a hard disk, solid state drive, flash drive, magnetic data storage medium, any optical or physical data storage medium, memory chip, or the like.

Storage media is distinct from but may be used in conjunction with transmission media. Transmission media participates in transferring information between storage media. For example, transmission media includes coaxial cables, copper wire and fiber optics, including the wires that comprise a bus of I/O subsystem 802. Transmission media can also take the form of acoustic or light waves, such as those generated during radio-wave and infra-red data communications.

Various forms of media may be involved in carrying at least one sequence of at least one instruction to processor 804 for execution. For example, the instructions may initially be carried on a magnetic disk or solid-state drive of a remote computer. The remote computer can load the instructions into its dynamic memory and send the instructions over a communication link such as a fiber optic or coaxial cable or telephone line using a modem. A modem or router local to computer system 800 can receive the data on the communication link and convert the data to a format that can be read by computer system 800. For instance, a receiver such as a radio frequency antenna or an infrared detector can receive the data carried in a wireless or optical signal and appropriate circuitry can provide the data to I/O subsystem 802 such as place the data on a bus. I/O subsystem 802 carries the data to memory 806, from which processor 804 retrieves and executes the instructions. The instructions received by memory 806 may optionally be stored on storage 810 either before or after execution by processor 804.

Computer system 800 also includes a communication interface 818 coupled to bus 802. Communication interface 818 provides a two-way data communication coupling to network link(s) 820 that are directly or indirectly connected to at least one communication networks, such as a network 822 or a public or private cloud on the Internet. For example, communication interface 818 may be an Ethernet networking interface, integrated-services digital network (ISDN) card, cable modem, satellite modem, or a modem to provide a data communication connection to a corresponding type of communications line, for example an Ethernet cable or a metal cable of any kind or a fiber-optic line or a telephone line. Network 822 broadly represents a local area network (LAN), wide-area network (WAN), campus network, internetwork or any combination thereof. Communication interface 818 may comprise a LAN card to provide a data communication connection to a compatible LAN, or a cellular radiotelephone interface that is wired to send or receive cellular radiotelephone data according to cellular radiotelephone wireless networking standards, or a satellite radio interface that is wired to send or receive digital data according to satellite wireless networking standards. In any such implementation, communication interface 818 sends and receives electrical, electromagnetic or optical signals over signal paths that carry digital data streams representing various types of information.

Network link 820 typically provides electrical, electromagnetic, or optical data communication directly or through at least one network to other data devices, using, for example, satellite, cellular, Wi-Fi, or BLUETOOTH technology. For example, network link 820 may provide a connection through a network 822 to a host computer 824.

Furthermore, network link 820 may provide a connection through network 822 or to other computing devices via internetworking devices and/or computers that are operated by an Internet Service Provider (ISP) 826. ISP 826 provides data communication services through a world-wide packet data communication network represented as internet 828. A server computer 830 may be coupled to internet 828. Server 830 broadly represents any computer, data center, virtual machine or virtual computing instance with or without a hypervisor, or computer executing a containerized program system such as DOCKER or KUBERNETES. Server 830 may represent an electronic digital service that is implemented using more than one computer or instance and that is accessed and used by transmitting web services requests, uniform resource locator (URL) strings with parameters in HTTP payloads, API calls, app services calls, or other service calls. Computer system 800 and server 830 may form elements of a distributed computing system that includes other computers, a processing cluster, server farm or other organization of computers that cooperate to perform tasks or execute applications or services. Server 830 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. Server 830 may comprise a web application server that hosts a presentation layer, application layer and data storage layer such as a relational database system using structured query language (SQL) or no SQL, an object store, a graph database, a flat file system or other data storage.

Computer system 800 can send messages and receive data and instructions, including program code, through the network(s), network link 820 and communication interface 818. In the Internet example, a server 830 might transmit a requested code for an application program through Internet 828, ISP 826, local network 822 and communication interface 818. The received code may be executed by processor 804 as it is received, and/or stored in storage 810, or other non-volatile storage for later execution.

The execution of instructions as described in this section may implement a process in the form of an instance of a computer program that is being executed, and consisting of program code and its current activity. Depending on the operating system (OS), a process may be made up of multiple threads of execution that execute instructions concurrently. In this context, a computer program is a passive collection of instructions, while a process may be the actual execution of those instructions. Several processes may be associated with the same program; for example, opening up several instances of the same program often means more than one process is being executed. Multitasking may be implemented to allow multiple processes to share processor 804. While each processor 804 or core of the processor executes a single task at a time, computer system 800 may be programmed to implement multitasking to allow each processor to switch between tasks that are being executed without having to wait for each task to finish. In an embodiment, switches may be performed when tasks perform input/output operations, when a task indicates that it can be switched, or on hardware interrupts. Time-sharing may be implemented to allow fast response for interactive user applications by rapidly performing context switches to provide the appearance of concurrent execution of multiple processes simultaneously. In an embodiment, for security and reliability, an operating system may prevent direct communication between independent processes, providing strictly mediated and controlled inter-process communication functionality.

The term "cloud computing" is generally used herein to describe a computing model which enables on-demand access to a shared pool of computing resources, such as computer networks, servers, software applications, and services, and which allows for rapid provisioning and release of resources with minimal management effort or service provider interaction.

A cloud computing environment (sometimes referred to as a cloud environment, or a cloud) can be implemented in a variety of different ways to best suit different requirements. For example, in a public cloud environment, the underlying computing infrastructure is owned by an organization that makes its cloud services available to other organizations or to the general public. In contrast, a private cloud environment is generally intended solely for use by, or within, a single organization. A community cloud is intended to be shared by several organizations within a community; while a hybrid cloud comprises two or more types of cloud (e.g., private, community, or public) that are bound together by data and application portability.

Generally, a cloud computing model enables some of those responsibilities which previously may have been provided by an organization's own information technology department, to instead be delivered as service layers within a cloud environment, for use by consumers (either within or external to the organization, according to the cloud's public/private nature). Depending on the particular implementation, the precise definition of components or features provided by or within each cloud service layer can vary, but common examples include: Software as a Service (SaaS), in which consumers use software applications that are running upon a cloud infrastructure, while a SaaS provider manages or controls the underlying cloud infrastructure and applications. Platform as a Service (PaaS), in which consumers can use software programming languages and development tools supported by a PaaS provider to develop, deploy, and otherwise control their own applications, while the PaaS provider manages or controls other aspects of the cloud environment (i.e., everything below the run-time execution environment). Infrastructure as a Service (IaaS), in which consumers can deploy and run arbitrary software applications, and/or provision processing, storage, networks, and other fundamental computing resources, while an IaaS provider manages or controls the underlying physical cloud infrastructure (i.e., everything below the operating system layer). Database as a Service (DBaaS) in which consumers use a database server or Database Management System that is running upon a cloud infrastructure, while a DbaaS provider manages or controls the underlying cloud infrastructure, applications, and servers, including one or more database servers.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A method for training a machine learning network for diagnostic quality assessment, the method comprising:
for each given training data pair of a plurality of training data pairs, where each given training data pair comprises at least a training text derived from a radiological report and a training image derived from a radiological exam image associated with the radiological report, training a diagnostic quality assessment machine learning network by:
determining, using a first encoder network, word embeddings for the training text;
generating, using a concept generator coupled to one or more layers of the first encoder network, a generated concept based on the operation of the one or more layers in determining the word embeddings;
regularizing the first encoder network by calculating a first loss between the generated concept and a labeled concept for the training text;
determining, using a second encoder network, features for the training image;
generating, using a heatmap generator coupled to one or more layers of the second encoder network, a generated heatmap based on the operation of the one or more layers in determining the features;
regularizing the second encoder network by calculating a second loss between the generated heatmap and a labeled heatmap for the training image;
classifying, via an error encoder, the given training data pair into a determined diagnostic quality category;
calculating a categorical cross entropy loss between the determined diagnostic quality category and a labeled diagnostic quality category for the given training data pair; and
minimizing a total loss function for the given training data pair, the total loss function comprising at least the first loss, the second loss, and the categorical cross entropy loss.

2. The method of claim 1, wherein the training text is a section of text obtained from a radiological report, wherein the section of text corresponds to an identified anatomical region or pathological feature discussed in the radiological report.

3. The method of claim 2, wherein the training image is a section obtained from a sequence of one or more radiological exam images from which the radiological report was prepared.

4. The method of claim 1, wherein for a given training data pair, the training text and the training image are associated with the same anatomical region or pathological feature.

5. The method of claim 4, wherein the same anatomical region or pathological feature is a motion segment of the lumbar spine.

6. The method of claim 1, wherein one or more of the plurality of training data pairs are obtained from a database of structured checklists corresponding to medical diagnostic data, the medical diagnostic data including radiological reports and radiological exam images.

7. The method of claim 1, wherein the first encoder network is configured as a recurrent neural network, an ordered neuron LSTM (Long short-term memory), or a Transformer based model trained specifically on a corpus of radiology report text.

8. The method of claim 1, wherein the labeled concept for a given training text includes an indication of one or more of: an identified pathology, a location of the identified pathology, and a severity of the identified pathology, as contained within the given training text.

9. The method of claim 1, wherein the second encoder network is a densely connected convolutional neural network (DenseNet) or a residual neural network (ResNet) adapted to the anisotropy and intensity distribution of radiology exam images.

10. The method of claim 1, wherein:
the generated heatmap is an attention heatmap determined from the one or more layers of the second encoder network while the second encoder network generates features for the training image; and
the labeled heatmap is an annotation corresponding to one or more anatomical features or pathological features as located within the training image.

11. The method of claim 1, wherein:
the heatmap generator comprises a decoder for performing a specific segmentation of the training image; and
the labeled heatmap is an annotated segmentation corresponding to one or more anatomical features or pathological features as located within the training image.

12. The method of claim 1, wherein the determined diagnostic quality category is selected from a set of diagnostic quality categories including 'Agree', 'Overcall', 'Undercall', and 'Missed'.

13. The method of claim 1, wherein training the diagnostic quality assessment machine learning network on the given training data pair further comprises:
regularizing the first encoder network by minimizing a first BCE (binary cross entropy) loss between a labeled pathology for the training text and a generated pathology for the training text, the generated text pathology output by an NLP (natural language processing) pathology classifier over the word embeddings of the first encoder network;
regularizing the second encoder network by minimizing a second BCE loss between a labeled pathology for the training image and a generated pathology for the training image, the generated image pathology output by an image pathology classifier over the features of the second encoder network; and
the total loss function further comprises the first BCE loss and the second BCE loss.

14. The method of claim 13, wherein:
the labeled pathology for the training text is ground-truth pathology information contained within the training text, independent from its specific textual expression; and
the labeled pathology for the training image is ground-truth pathology information present in the training image, wherein the ground-truth pathology information for a given training image is determined as a consensus obtained from one or more expert reviews of the given training image.

15. The method of claim 14, wherein the labeled pathology for the training image is generated automatically based on accessing one or more structured checklists generated in response to receiving a user input representing of the one or more expert reviews of the given training image.

16. The method of claim 1, wherein training the diagnostic quality assessment machine learning network on the given training data pair further comprises:
providing, to a Siamese function, an input comprising the word embeddings determined for the training text by the first encoder network and the image features determined for the training image by the second encoder network;
calculating, using the Siamese function, a Siamese distance between the word embeddings and the image features;
calculating, using a Siamese error encoder, a Siamese loss between the Siamese distance and a Siamese label, the Siamese label indicating an extent to which the training text and training image of the given training data pair agree or disagree; and
minimizing the Siamese loss to increase a distance between training text and training images that disagree and to decrease a distance between training text and training images that agree.

17. The method of claim 16, wherein:
the Siamese loss is a multi-task loss;
the error encoder classifies the given training data pair into the determined diagnostic quality category based at least in part on the Siamese distance output by the Siamese function; and
the total loss function for the given training data pair further includes the Siamese loss.

18. The method of claim 16, further comprising:
back propagating the Siamese loss to adjust one or more parameters of the first encoder network and the second encoder network; and
configuring the Siamese error encoder as a controller to the error encoder, wherein the error encoder classifies the given training data pair into the determined diagnostic quality category based on the word embeddings from the first encoder network and the image features from the second encoder network.

19. The method of claim 18, wherein the Siamese error encoder acts as a controller to the error encoder by causing the error encoder to regress to an estimated diagnostic error on the basis of the Siamese distance between the word embeddings and the image features.

20. The method of claim 1, further comprising:
providing at least the determined diagnostic error from the error encoder, the word embeddings from the first encoder network, and the image features from the second encoder network, to a clinical significance encoder; and
regressing, using the clinical significance encoder, to an estimated clinical significance of the determined diagnostic error, wherein the clinical significance encoder is configured as a regressor network having a sigmoid activation function.

21. The method of claim 1, further comprising:

providing one or more clinical references to a clinical controller of the diagnostic quality assessment machine learning network, the clinical references including one or more of patient age, patient weight, and patient history of previous related pathologies; and generating, from the one or more clinical references and via the clinical controller, a feature vector to control the second encoder network.

* * * * *